(12) United States Patent
Schoess et al.

(10) Patent No.: US 10,531,977 B2
(45) Date of Patent: Jan. 14, 2020

(54) THERMORESPONSIVE SKIN BARRIER APPLIANCES

(71) Applicant: Coloplast A/S, Humlebaek OT (DK)

(72) Inventors: Jeffrey Norman Schoess, Howard Lake, MN (US); Kannan Sivaprakasam, St. Cloud, MN (US)

(73) Assignee: Coloplast A/S, Humlebaek (DK)

( * ) Notice: Subject to any disclaimer, the term of this patent is extended or adjusted under 35 U.S.C. 154(b) by 853 days.

(21) Appl. No.: 14/690,324

(22) Filed: Apr. 17, 2015

(65) Prior Publication Data

US 2019/0142623 A1     May 16, 2019

Related U.S. Application Data

(60) Provisional application No. 61/981,020, filed on Apr. 17, 2014.

(51) Int. Cl.
*A61F 5/443* (2006.01)
*A61F 5/44* (2006.01)
*A61F 5/445* (2006.01)

(52) U.S. Cl.
CPC ............ *A61F 5/443* (2013.01); *A61F 5/4404* (2013.01); *A61F 5/445* (2013.01)

(58) Field of Classification Search
CPC ........ A61F 5/443; A61F 5/4404; A61F 5/445; A61F 5/448; A61F 5/44; A61F 13/42; A61F 13/421; A61F 13/424; A61F 13/427; A61F 13/443
See application file for complete search history.

(56) References Cited

U.S. PATENT DOCUMENTS

| | | |
|---|---|---|
| 3,832,510 A | 8/1974 | Pfau et al. |
| 4,754,264 A | 6/1988 | Okada et al. |
| 4,982,742 A | 1/1991 | Claude |
| 5,016,645 A | 5/1991 | Williams et al. |
| 5,593,397 A | 1/1997 | La Gro |

(Continued)

FOREIGN PATENT DOCUMENTS

| | | |
|---|---|---|
| CN | 104902399 A | 9/2015 |
| CN | 104980878 A | 10/2015 |

(Continued)

OTHER PUBLICATIONS

Self-Sealing Therapy (Self-Sealing Therapy Ostomy Pouch, https://www.sbir.gov/sbirsearch/detail/5517, accessed Feb. 21, 2018, captured Oct. 20, 2011).*

(Continued)

*Primary Examiner* — Ariana Zimbouski
(74) *Attorney, Agent, or Firm* — Coloplast Corp., Coloplast A/S; Nick Baumann

(57) ABSTRACT

Thermoresponsive skin barrier assemblies are disclosed. One such wound treatment assembly includes a pump configured to expel a biosealant to a pump output port when subjected to a thermal stimulus, and an adhesive substrate layer for covering the wound. The adhesive substrate layer includes a conduit configured to transport the biosealant from the output port to the wound. The assembly further includes a control module in signal communication with a wound leakage sensor configured to activate a heating element disposed in proximity to the pump when wound leakage is detected.

7 Claims, 25 Drawing Sheets

(56) References Cited

U.S. PATENT DOCUMENTS

| | | | |
|---|---|---|---|
| 5,677,221 | A | 10/1997 | Tseng |
| 5,834,009 | A | 11/1998 | Sawers et al. |
| 5,879,292 | A | 3/1999 | Sternberg et al. |
| 6,025,725 | A | 2/2000 | Gershenfeld et al. |
| 6,103,033 | A | 8/2000 | Say et al. |
| 6,171,289 | B1 * | 1/2001 | Millot .................... A61F 5/443 604/336 |
| 6,433,244 | B1 * | 8/2002 | Roe .......................... A61F 13/42 604/359 |
| 7,199,501 | B2 | 4/2007 | Pei et al. |
| 7,670,289 | B1 | 3/2010 | McCall |
| 8,398,603 | B2 | 3/2013 | Thirstrup et al. |
| 8,409,158 | B2 | 4/2013 | Edvardsen et al. |
| 9,046,085 | B2 * | 6/2015 | Schoess ................ F04B 19/006 |
| 9,216,104 | B2 | 12/2015 | Thirstrup et al. |
| 9,322,797 | B1 | 4/2016 | Lastinger et al. |
| 10,016,298 | B2 | 7/2018 | Thirstrup et al. |
| 2002/0019615 | A1 | 2/2002 | Roe et al. |
| 2003/0132763 | A1 | 7/2003 | Ellenz |
| 2003/0169032 | A1 | 9/2003 | Minchole et al. |
| 2004/0036484 | A1 | 2/2004 | Tamai |
| 2004/0133175 | A1 | 7/2004 | Hagedorn-Olsen |
| 2007/0135782 | A1 | 6/2007 | Bager et al. |
| 2007/0185464 | A1 | 8/2007 | Fattman et al. |
| 2008/0075934 | A1 | 3/2008 | Barlow, Jr. et al. |
| 2008/0140057 | A1 * | 6/2008 | Wood ................ A61M 5/14276 604/891.1 |
| 2008/0300559 | A1 | 12/2008 | Gustafson et al. |
| 2009/0173935 | A1 | 7/2009 | Cho et al. |
| 2010/0030167 | A1 | 2/2010 | Thirstrup et al. |
| 2011/0077497 | A1 | 3/2011 | Oster et al. |
| 2012/0013130 | A1 | 1/2012 | Jung |
| 2012/0143155 | A1 | 6/2012 | Edvardsen et al. |
| 2012/0258302 | A1 | 10/2012 | Hunt et al. |
| 2013/0231620 | A1 | 9/2013 | Thirstrup et al. |
| 2014/0200538 | A1 * | 7/2014 | Euliano .................. A61F 13/42 604/361 |
| 2015/0231802 | A1 | 8/2015 | Quan et al. |
| 2015/0250639 | A1 | 9/2015 | Thirstrup et al. |
| 2015/0257923 | A1 | 9/2015 | Thirstrup et al. |
| 2016/0158969 | A1 | 6/2016 | McLane et al. |

FOREIGN PATENT DOCUMENTS

| | | |
|---|---|---|
| CN | 105588856 A | 5/2016 |
| DE | 19953062 A1 | 5/2000 |
| EP | 0850076 B1 | 4/2005 |
| EP | 1188157 B1 | 12/2005 |
| EP | 2489561 A2 | 8/2012 |
| GB | 2343628 A | 5/2000 |
| GB | 2542093 A | 3/2017 |
| TW | 201201783 A | 1/2012 |
| WO | 9415562 A1 | 7/1994 |
| WO | 0079497 A1 | 12/2000 |
| WO | 02052302 A2 | 7/2002 |
| WO | 02099765 A1 | 12/2002 |
| WO | 2007098762 A1 | 9/2007 |
| WO | 2009052496 A1 | 4/2009 |
| WO | 11105701 A2 | 9/2011 |
| WO | 2011161254 A2 | 12/2011 |
| WO | 2014004207 A1 | 1/2014 |
| WO | 2015014774 A1 | 2/2015 |

OTHER PUBLICATIONS

Office Action dated May 26, 2015 in U.S. Appl. No. 13/769,393.
Office Action dated Dec. 17, 2015 in U.S. Appl. No. 14/630,670.
Office Action dated Nov. 30, 2016 in U.S. Appl. No. 14/630,670.
Office Action dated Mar. 21, 2019 in U.S. Appl. No. 14/630,669.
Burns et al. "Inkjet Printing of Polymer Thin-Film Transistor Circuits" MRS Bulletin, 2003, vol. 28 No. 11, pp. 829-834.
"Ultra-Low-Power, Single-Supply Op Amp + Comparator + Reference" Maxim Integrated Products, 2001, pp. 1-12.
Ignjatovic et al. "An Interface Circuit for Measuring Capacitance Changes Based Upon Capacitance-to-Duty Cycle (CDC) Converter" IEEE Sensors Journal, 2005, vol. 5 No. 3, pp. 403-405.
Akar et al. "A wireless batch sealed absolute capacitive pressure sensor" Sensors and Actuators A, 2001, vol. 95, pp. 29-38.
Zeng et al. "Time domain characterization of oscillating sensors: Application of frequency counting to resonance frequency determination" Review of scientific instruments, 2002, vol. 73 No. 12, pp. 4375-4380.
Ong et al. "Design and application of a wireless, passive, resonant-circuit environmental monitoring sensor" Sensors and Actuators A, 2001, vol. 93, pp. 33-43.
Ashrafi et al. "A high precision method for measuring very small capacitance changes" Review of scientific instruments, 1999, vol. 70 No. 8, pp. 3483-3487.

* cited by examiner

| Sample | Pressure at 120 s (psi) | initial sample mass (g) | thickness (mm) |
|---|---|---|---|
| D-IPN Dec'14 2-3 | 4.71 | 0.1073 | 3.23 |
| D-IPN Dec'14 2-2 | 5.01 | 0.1067 | 3.23 |
| D-IPN Dec'14 2-1 | 4.98 | 0.1338 | 4.05 |
| D-IPN Dec'14 1-2 | 0.87 | 0.101 | 3.47 |
| D-IPN Dec'14 1-1 | | 0.1023 | 3.49 |
| D-IPN Nov'14 3-4 | | 0.0928 | 3.47 |
| D-IPN Nov'14 3-3 | 0.219 | 0.0948 | 3.47 |
| D-IPN Nov'14 3-2 | 2.27 | 0.1158 | 3.31 |
| D-IPN Nov'14 3-1 | 2.65 | 0.1214 | 3.4 |
| D-IPN Nov'14 2-4 | 0.92 | 0.0619 | 3.46 |
| D-IPN Nov'14 1-5 | 1.968 | 0.0639 | 2.42 |
| D-IPN Nov'14 1-4 | 2.37 | 0.0829 | 3.45 |
| D-IPN Nov'14 2-2 | 3.62 | 0.0875 | 3.49 |
| D-IPN Nov'14 2-1 | 6.779 | 0.0962 | 3.49 |
| D-IPN Nov'14 1-3 | 5.41 | 0.0919 | 3.46 |
| D-IPN Nov'14 1-1 | 2.16 | 0.1207 | 3.46 |

TABLE 1

FIG. 27

THERMORESPONSIVE SKIN BARRIER APPLIANCES

CROSS REFERENCE TO RELATED APPLICATIONS

This application claims priority to and the benefit under 35 USC § 119(e) of U.S. Provisional Patent Application No. 61/981,020, filed on Apr. 17, 2014, the contents of which are incorporated by reference in their entirety as if fully set forth herein.

STATEMENT REGARDING FEDERALLY SPONSORED RESEARCH OR DEVELOPMENT

Research and development of the concepts disclosed herein were funded in part by grants from the National Institutes of Health, Grant Nos. 1R43RR025266-01A2, 1R43 RR016122-01, 2R43 RR016122-02 and 1R43 RR025266-01. The United States Government may have certain rights to the disclosed subject matter.

TECHNICAL FIELD

This disclosure relates to systems and methods for thermoresponsive, wearable skin barriers. In particular, this disclosure relates to thermoresponsive ostomy skin barrier appliances that are capable of sensing stoma leakage and responding by deploying an amount of sealant to prevent further leakage from a miniature pump system.

BACKGROUND

An ostomy generally refers to a surgically created opening in the body for the discharge of body wastes. Over one million ostomy surgeries are performed each year, which generally involve routing a resectioned or missing intestine or urinary tract to a surgeon-created opening in the patient's abdomen. Patients who have undergone an ostomy procedure can require emotional care in addition to the physical attention needed to prevent infection, leakage, and other physiological concerns.

In many cases, an ostomy appliance can be used for both sealing the ostomy and collecting bodily waste therefrom. Maintaining an effective appliance seal can be critical to physical and emotional well-being of an individual with an ostomy. In some cases, an ineffective seal can lead to a cycle of misery for the ostomy patient. Leakage around the ostomy site can cause the breakdown of surrounding skin tissue, which can cause further leakage and perpetuate the cycle.

Ostomy leakage can be caused by a number of factors, including dermatitis caused by leakage, trauma, stripping, or exposure or sensitivity to chemicals for bonding an ostomy appliance to the skin; leakage due to the construction or design of the appliance; poor placement, inadequate fit; yeast infections; and disease caused by, e.g., radiation exposure and infection, including *Pyoderma Gangrenosum*; among others.

One clinical study showed that 73% of subjects with intestinal ostomies (65% colostomy, 35% ileostomy patients) experienced leakage where 23% of those subjects were identified as having "severe" leakage (Lyon C C, Smith A J, Griffiths C E M, Beck M H, *The spectrum of skin disorders in abdominal stoma patients*, British J of Dermatology, 143(6):1248-1260, 2001). The study inferred that the leakage caused a reduction in quality of life, with 66% experiencing difficulty in adjusting (having an ostomy for more than five years) and 70% experiencing skin problems. In the same study 26% of the subjects reported embarrassment due to leakage, odor, and noise, which lead to higher levels of anxiety and depression, difficulty with intimacy, and a feeling of isolation.

SUMMARY

In general, thermoresponsive skin barrier appliances are disclosed. In one exemplary embodiment, a thermoresponsive skin barrier appliance includes a pump configured to expel a biosealant to a pump output port when subjected to a thermal stimulus, and an adhesive substrate layer for covering the wound. The adhesive substrate layer includes a conduit configured to transport the biosealant from the output port to the wound. The assembly further includes a control module in signal communication with a wound leakage sensor configured to activate a heating element disposed in proximity to the pump when wound leakage is detected.

Ineffective ostomy seals can lead to leakage which can cause skin breakdown and further leakage. The likelihood of leakage can be minimized by early detection of leakage via electrochemical sensing, informing the patient to take corrective action before leakage occurs via one or more alerting modalities, and providing additional protection to prevent or reduce leakage by dispensing of a biocompatible adhesive sealant to the ostomy site.

In one exemplary aspect, a pump is disclosed. The pump includes a first pump body having a chamber for storing a flowable substance and one or more exit ports in fluid communication with the chamber, through which the flowable substance can be dispensed when the pump is activated. The pump further includes a flexible diaphragm sealingly engaged to the first pump body and positioned to retain the flowable substance within the chamber when the pump is in a pre-activation configuration, and a layer of absorbent material disposed upon a surface of the diaphragm opposite the chamber. A second pump body is sealingly engaged to the first pump body having first and second chambers and is connected by a porous wall that, when the pump is activated, allows a stored activation fluid to flow from the first chamber through the second chamber, and onto the layer of absorbent material to cause the layer of absorbent material to swell in size. Swelling of the absorbent material causes the diaphragm to flex into the first pump body chamber and thereby urge the flowable substance toward the one or more exit ports. A pump output rate can be determined by a moisture content of the absorbent material.

In one exemplary aspect, a pump for dispensing a stored fluid, gas or gel is described. The pump includes a pump body having a first fluid-retaining chamber for retaining the stored fluid, gas or gel defined by one or more inner walls, a floor adjacent to the one or more inner walls, and a flexible diaphragm, wherein the flexible diaphragm is capable of extending into the fluid retaining chamber under an urging force provided by expansion of an absorbent material layer disposed on a surface of the diaphragm opposite of the fluid-retaining chamber to cause the fluid, gas or gel to be dispensed from the pump body through one or more exit channels that extend from the chamber to an exterior portion of the pump body. The pump further includes a pump activator including an activation solution contained in a storage chamber capable of causing the absorbent material layer to expand in volume when received and absorbed by the absorbent material layer, and a plug layer interposed between the storage chamber and the absorbent material layer capable of substantially preventing the activation solution from contacting the absorbent material layer under a first environmental condition, and allowing the activation solution to flow to the absorbent material layer under a second, different environmental condition. A pump output rate is determined by a moisture content of the absorbent material.

In a first exemplary aspect, a thermoresponsive skin barrier appliance is disclosed. The appliance includes a micropump, which itself includes a first pump body having a chamber for storing a flowable substance and one or more exit ports in fluid communication with the chamber, through which the flowable substance can be dispensed when the pump is activated, a flexible diaphragm sealingly engaged to the first pump body and positioned to retain the flowable substance within the chamber when the pump is in a pre-activation configuration, a layer of absorbent material disposed upon a surface of the diaphragm opposite the chamber, and a second pump body sealingly engaged to the first pump body having first and second chambers connected by a porous wall that, when the pump is activated, allows a stored activation fluid to flow from the first chamber through the second chamber, and onto the layer of absorbent material to cause the layer of absorbent material to swell in size. Swelling of the absorbent material causes the diaphragm to flex into the first pump body chamber and thereby urge the flowable substance toward the one or more exit ports. The appliance further includes a moisture sensor in signal communication with the micropump.

In one embodiment, the moisture sensor is configured to activate the pump.

In one embodiment, the moisture sensor is capable of sensing effluent flow in substantially orthogonal flow directions. In a related embodiment, the moisture sensor includes a first electrochemical array configured to detect moisture in a first flow propagation direction, and a second electrochemical array configured to detect moisture in a second, different flow propagation.

In one embodiment, the moisture sensor is disposed between upper and lower layers of a fluid permeable material layer. In a related embodiment, the material layer includes a hydrocolloid.

In one embodiment, a microchannel array provides a fluid conduit between the one or more exit ports of the micropump and a target delivery site for the flowable substance.

In one embodiment, the moisture sensor is configured to sense a biological fluid emanating from a stoma. In a related embodiment, the flowable substance is an adhesive capable of providing a seal which stops emanation of the biological fluid from the stoma. In yet another related embodiment, the appliance further includes a coupler configured to engage an ostomy bag.

In one exemplary aspect, a thermoresponsive skin barrier appliance is disclosed. The appliance includes a moisture sensor disposed between upper and lower hydrocolloid layers configured to detect moisture and send an activation signal to a pump containing a flowable substance upon the detection of the moisture, and the moisture sensor is configured to detect moisture flow in either of two substantially orthogonal moisture flow directions.

In one embodiment, the moisture sensor includes at least two electrochemical sensors configured to detect the moisture.

In one embodiment, the flowable substance is a sealant or a therapeutic compound.

In one embodiment, the appliance further includes a microchannel array configured to provide a flow path for the flowable substance between an output of the pump and a target delivery area.

In one embodiment, the appliance further includes an expandable fluid delivery channel formed from at least two overlapping sheets of a polymeric material. In a related embodiment, a proximal end portion of the fluid delivery channel includes an input port for receiving the flowable substance, and a distal end portion of the fluid delivery channel includes an output port for dispensing the flowable substance onto a target area.

In one embodiment, the appliance further includes a user-activated control module for activating the pump to expel the flowable substance on demand.

In a second exemplary aspect, a thermoresponsive skin barrier appliance is provided. The appliance includes a pump providing a source of a flowable sealant and is configured with a moisture detector for detecting a flow of moisture and correspondingly triggering the pump to dispense the flowable sealant.

In a third exemplary aspect, a thermoresponsive skin barrier appliance is described. The appliance includes a pump configured to expel a biosealant to a pump output port when subjected to a thermal stimulus, an adhesive substrate layer for covering the wound including a conduit configured to transport the biosealant from the output port to the wound, and a control module in signal communication with a wound leakage sensor configured to activate a heating element disposed in proximity to the pump when wound leakage is detected.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings, which may not necessarily be to scale, in which like references indicate similar elements, and in which:

FIG. 27 shows that hydrogel beads having at least some moisture content, i.e., prior to being exposed to the activation solution, results in a faster, higher pressure pump output rate than dry hydrogel beads.

DETAILED DESCRIPTION OF ILLUSTRATIVE EMBODIMENTS

In the description that follows, pump assemblies or simply "pumps" or "micropumps" are referred to. Co-pending U.S. patent application Ser. No. 13/601,809 filed Aug. 31, 2012 and entitled "Miniature Pumps" by Jeffrey N. Schoess and Kannan Sivaprakasam describes miniature pumps that can be utilized for the miniature pump assemblies referred to herein, in whole or in part. U.S. patent application Ser. No. 13/601,809 is therefore incorporated by reference for all purposes as if fully set forth herein.

In one aspect, pumps are described that are capable of controllably flowing a stored medium, e.g., a liquid, gel, or gas, from a retaining tub, bin, capsule, or other type of container upon application of an external stimulus to the pump. External stimuli can include, without limitation, application of: heat or cold, magnetic fields, vibration, light energy, exposure to changes in pH or salinity, or other stimuli. Thus, in the description that follows, such pumps can be selectively activated without the need for an external power source such as a battery or electrical current from an outlet source.

Figure 1A:
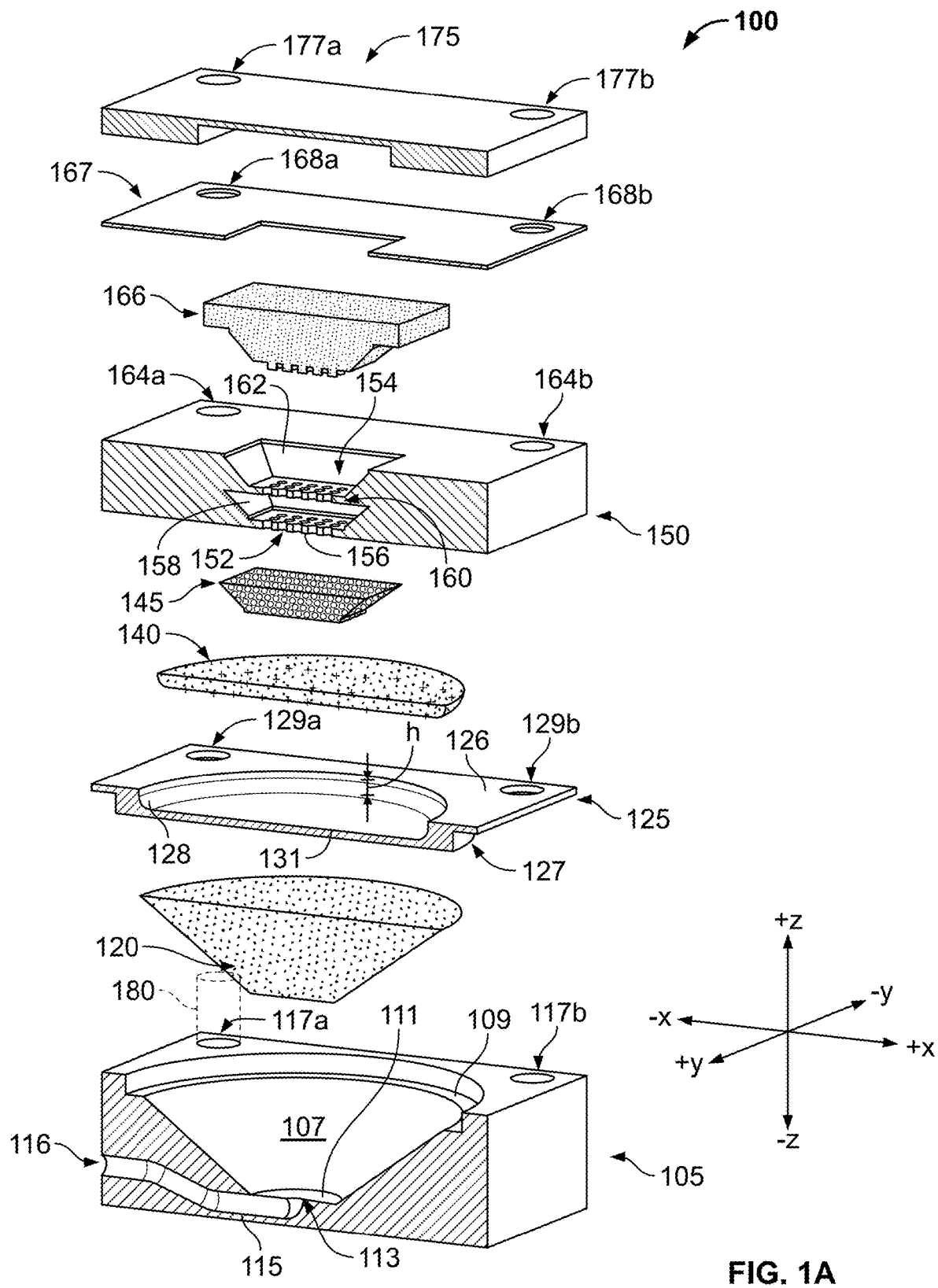
FIG. 1A is a half-section, exploded-view of a pump, according to one embodiment.
Figure 1B:
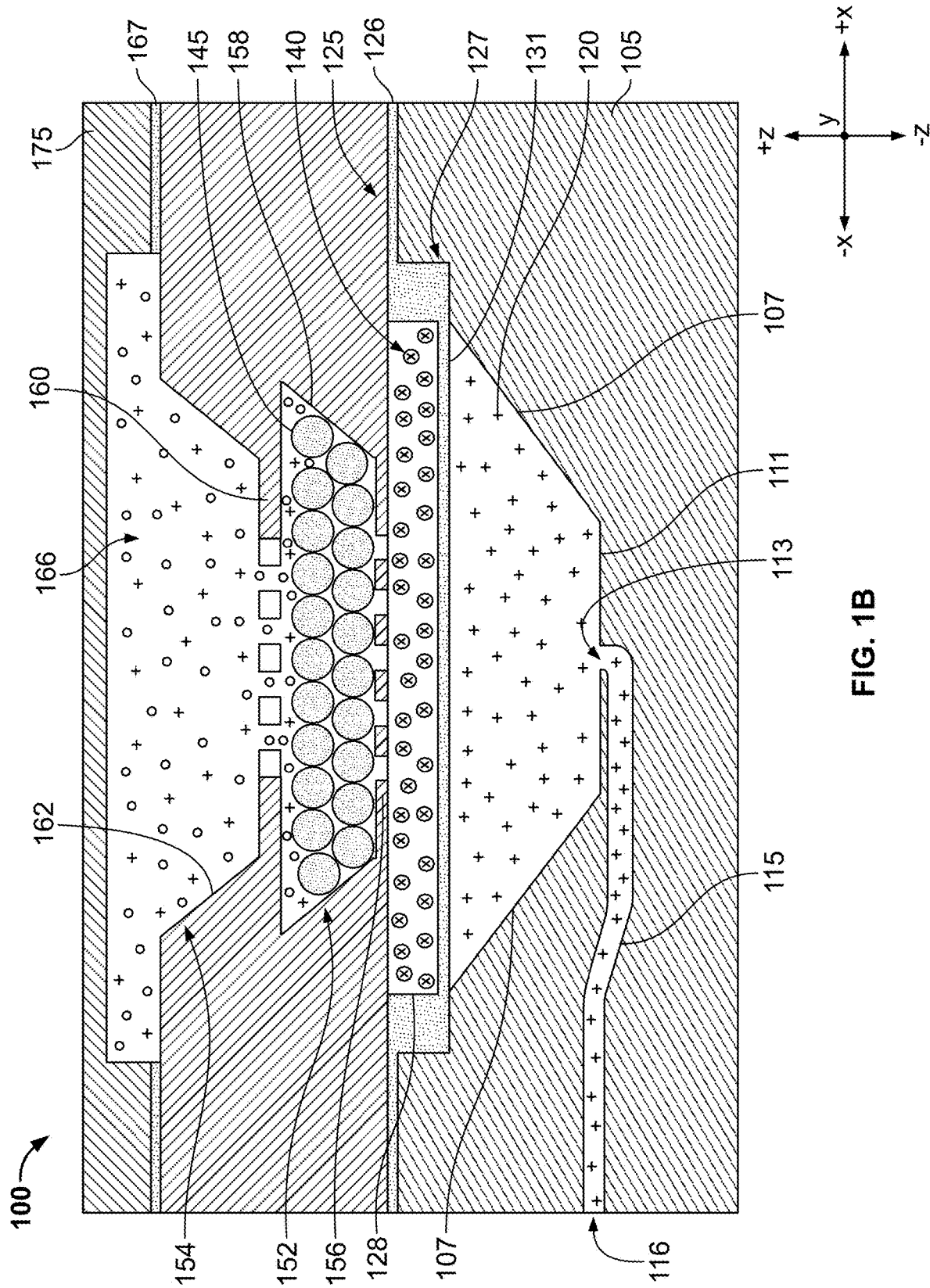
FIG. 1B is a cross-sectional view of the assembled pump shown in FIG. 1A, according to one embodiment.

FIGS. 1A and 1B illustrate a pump 100 according to one embodiment. FIG. 1A is a half-section, exploded-view of the pump 100 shown divided through the x-z plane. FIG. 1B illustrates the pump 100 in an operative, assembled configuration, according to one embodiment. Throughout the following description, like references in FIGS. 1A and 1B indicate similar elements.

In this embodiment, the pump 100 includes a lower pump body 105. The lower pump body 105 includes an inner wall 107 that defines a substantially conical-shaped cavity within the interior of the lower pump body 105 as shown. In this embodiment, the lower pump body 105 is composed of poly(methyl methacrylate) (PMMA); however, other suitable materials can be substituted according to preference. In this embodiment, a disc-shaped floor 111 abuts the inner wall 107 and defines a base of the substantially conical-shaped cavity. The floor 111 includes an aperture 113 that defines one end of a hollow passage 115; the passage 115 is a conduit for transmitting a dispensable fluid 120 from the conical-shaped cavity to an exterior outlet port 116. While reference is made to "fluid" in the description of this and other embodiments, it will be understood that fluids, gels, gasses, and other materials capable of being flowed are equally contemplated, even though they may be classified as other than fluids in the strictest scientific interpretations.

In this and other embodiments, the dispensable fluid 120 can be any substance capable of being flowed from one location (e.g., the conical-shaped cavity) to another location (e.g., to the exterior outlet port 116), including, but not limited to fluids, gels, and gasses. For instance, the dispensable fluid 120 can be a solution that includes one or more therapeutic dose(s) of: a pharmacological agent; an antibiotic; a solution containing one or more compounds for treating wounds, ailments, or other afflictions; a sealant; a solution for irrigating or flushing exudates or neurotic tissue, or other therapeutic solutions. The dispensable fluid can be, e.g., a gel, including therapeutic gels; an oil; a hydrocarbon or a derivative thereof; a chemotherapeutic agent that includes a platelet-derived growth factor fluid to stimulate blood vessel formation and tissue cell growth; a saline solution; water; or other fluids, gels, or gasses. In some cases, the surfaces of the conical-shaped cavity, e.g., inner wall 107, floor 111, etc., can be coated with materials to prevent reaction of the dispensable fluid 120 with the lower pump body 105 material composition.

In this and other embodiments, the dispensable fluid 120 can be a fluid for positioning or separation of internal tissues in an animal subject, such as a viscous polymer or polysaccharide solution. In one example of such an embodiment, the dispensable fluid 120 can be formulated to reduce the likelihood of pre- or post-surgical adhesions in reproductive system tissues, abdominal and bowel tissues, ophthalmic tissues, or skeletal joint and muscle tissues. In another example, the dispensable fluid 120 can be a fluid formulated to reduce the likelihood of tendons binding to tendon sheaths, which can be found, for example, within the physiology of the human hand. In another example, the dispensable fluid 120 can be a fluid formulated to position ophthalmic tissues and maintain those positions during tissue healing; one such fluid is described in U.S. Pat. No. 5,207,660, filed Apr. 26, 1991 to Harvey A. Lincoff, entitled "Method for Delivery of Compositions to Ocular Tissues," which is incorporated by reference herein in its entirety for all purposes. In yet another example, the dispensable fluid 120 can be a fluid formulated to coat tissue such as bladder tissue in an animal subject, to treat or reduce the likelihood of interstitial cystitis. Those skilled in the art will appreciate that other dispensable fluids 120 can be used according to an intended application of the pump 100.

In this and other embodiments, a plug, one-way valve, or other flow-restriction device (not shown in FIG. 1A or 1B) can be used for preventing the dispensable fluid 120 from flowing out of the lower pump body 105 prior to activation of the pump, which is described in greater detail below. In some embodiments, the aperture 113 can lead to an exit port (e.g., the exit port 213 shown in FIG. 2) that allows the dispensable fluid 120 to exit the lower pump body 105 directly, e.g., through a vertical bore (not shown in FIG. 1A or 1B). In such cases the lower pump body 105 can be configured to include attachment mechanisms for receiving a tube or other or lumen-like structure capable of carrying the dispensable fluid 120 from the pump 100. In other such cases, the vertical bore can include interior threads for receiving an end portion of a tube or other fluid-carrying structure having complimentary exterior threads; thus, the end portion of the tube can be screwed into the vertical bore to create a reversible union therebetween. In one embodiment, the vertical bore can be configured as a plunger and configured to receive an extender tube. The extender tube can carry the dispensable fluid 120 from the pump 100 to a chosen location. For example, the extender tube can include a distal tapered nozzle end portion configured to be inserted into tissue, a hydrocolloid dressing or wafer, an object intended to be lubricated by the dispensable fluid 120, or a fluid port.

In this embodiment, the lower pump body 105 includes bores 117a, 117b configured to receive a portion of a fastener that couples other parts of the pump together, as described in greater detail below (other bores may be included on the portion of the lower pump body 105 not illustrated in FIG. 1A or 1B). Exemplary fasteners include, but are not limited to: bolts, clamps, couplings, dowels, screws, such as machine screws, pop rivets, and other fasteners known in the art. In other embodiments, the components of the pump can be assembled and secured into place using glues, cements, or other adhesives.

In this embodiment, the top of the inner wall 107, i.e., the portion of the wall 107 where the circular diameter is greatest in the x-y plane is adjacent to a surrounding platform portion 109 that is configured to sealingly engage with a complimentary shoulder 127 of a flange member 125 (described in greater detail below). The sealing engagement between the platform portion 109 and the flange member 125 caps the conical-shaped portion and can provide the capability for storing the dispensable fluid 120 within the lower pump body 105.

In this embodiment, the pump 100 further includes a flange member 125. The flange member 125 includes the aforementioned shoulder 127, which generally protrudes downwardly (in the −z direction, as shown) from a top surface 126 to sealingly engage with the platform portion 109 of the lower pump body 105. The flange member 125 further includes apertures 129a, 129b configured and positioned so as to overlap with bores 117a, 117b of the lower pump body 105 when sealingly engaged thereto.

In this embodiment, the shoulder 127 of the flange member 125 supports a disk-shaped, resiliently-flexible diaphragm 131. The diaphragm 131 is generally able to resiliently flex or stretch in +/−z directions according to the frame of reference provided by FIGS. 1A and 1B. During operation of the pump, which is described in greater detail below, the diaphragm 131 can expand, e.g., under applied force, into the conical-shaped cavity of the lower pump body 105, thereby urging the dispensable fluid 120 into the aperture 113 of the hollow passage 115.

In this embodiment, the diaphragm 131 is a flexible elastomeric membrane composed of silicone rubber, although other suitable alternative materials can be substituted according to preference. Suitable alternative membrane compositions include, without limitation: silicone rubber polymer, latex rubber, fluoroelastomers such as Viton™ sold by DuPont Performance Elastomers LLC, perfluoroelastomers, PTFE, polyester, polyethylene, and polyurethane; other flexible membrane materials can be substituted according to preference or for a particular use. The thickness of the diaphragm 131 can be chosen to provide a desired amount of elasticity, which, as explained in greater detail below, can influence the rate and amount of dispensable fluid 120 that is expelled from the pump 100 when the pump is activated. Without wishing to be bound by theory, when the pump 100 is activated, a diaphragm 131 having a higher degree of elasticity can be expected to encroach further and faster into the conical-shaped cavity of the lower pump body 105 than a diaphragm 131 having a lesser degree of elasticity, assuming an equal amount of urging force in both cases.

In this embodiment, a polymer layer 140 occupies a substantially disk-shaped void that is defined in part by the downward (−z direction) protrusion of the shoulder 127 from the plane of the top surface 126 of the flange 125. The empty volume of the substantially disk-shaped void, which can also define the volume of the polymer layer 140 if completely full, is defined in part by the height h of the inner shoulder rim 128; the height h (and thereby the amount of polymer 140 used in various embodiments) can be chosen according to preference and functional considerations as described herein. In general, the polymer layer 140 can include a polymer composition capable of absorbing fluid so as to increase the volume of the polymer layer 140 from a first volume to a second, larger volume. In some embodiments, the polymer can be capable of absorbing fluid to increase the volume of the polymer layer 140 from a first volume to a second, larger volume, and subsequently releasing fluid to return to approximately the first volume. Exemplary polymers for this purpose include, without limitation, the class of polymers generally known as superporous hydrogels (SPH's). SPH polymers or SPH polymer compositions can be applied as a paste, foam layer, or solid layer on the top surface of the diaphragm (e.g., the diaphragm surface proximal to the top surface 126 of the flange 125).

In this and other embodiments, a base hydrogel polymer capable of absorbing water or other solutions (including solution 166 described below) can be synthesized by combining at least one ethylenically-unsaturated hydrophilic monomer, a multi-olefinic crosslinking agent and a strengthening agent, which can occupy the narrow spaces of the base polymer matrix. Exemplary ethylenically-unsaturated hydrophilic monomers for this purpose include acrylamide (AM), sulfopropylacrylate (SPAK) and hydroxyl ethylmethacrylate (HEMA), although other ethylenically-unsaturated hydrophilic monomers can be substituted according to preference or for a particular use. In one example, methylene bisacrylamide (BIS) can be used as a multi-olefinic crosslinking agent, although other crosslinking agents can be used. In a preferred embodiment, the strengtheners are polysaccharides which can include polymers of alginic acid, chitosan, carboxymethylcellulose (and its derivatives), (meth)acrylate derivatives (e.g., methyl, ethyl, butyl), polyacetonitrile (PAN), and natural or synthetic rubber emulsions, although other strengtheners can be used. In one embodiment, a superporous hydrogel has an average pore size between about 100 µm and about 600 µm. In general, and without wishing to be bound by theory, it is believed that the presence of large pores in the SPH can contribute to rapid, large-volume absorption of fluids, which can be advantageous in the operational characteristics of some pump embodiments, e.g., rapid expulsion of the dispensable fluid 120.

Some SPH's and SPH compositions are known to swell when exposed to certain fluids, in some cases increasing their volume by a factor of 50 to 200. Exemplary SPH's that can be used in embodiments described herein, including variations thereof, include the hydrogel compositions described in U.S. Pat. No. 6,271,278 to Kinam Park, filed May 13, 1997; U.S. Pat. No. 6,960,617 to Hossein Omidian et al., filed Apr. 22, 2003; and U.S. Pat. No. 7,988,992 also to Hossein Omidian et al., filed Jul. 6, 2007. U.S. Pat. Nos. 6,271,278, 6,960,617 and 7,988,992 are incorporated by reference herein in their entirety for all purposes.

One exemplary, commercially-available microsphere SPH that can be used in the polymer layer 140 is sold under the Expancel brand (Akzo Nobel, Sundsvall, Sweden). Expancel beads can be on the order of 5-10 µm in diameter at ambient temperature (e.g., room temperature). In one embodiment, a polymer layer 140 can be formed into a malleable paste by mixing Expancel microspheres with glycerin, and screen-printing the resulting paste on to the diaphragm layer. Glycerin can be a preferred mixing agent for supporting the SPH's due to its thermal conductivity characteristics and high boiling point, which can reduce the likelihood of evaporation of the paste.

In this embodiment, the pump 100 further includes an upper pump body 150. The upper pump body 150 includes a lower basket 152 and an upper basket 154, each having a truncated square pyramid shape, as shown, which are defined in part by lower basket interior wall 158 and lower basket floor 156, and upper basket interior wall 162 and upper basket floor 160, respectively. (The other walls defining the truncated square pyramid shape are not labeled in FIG. 1 for clarity.) In this embodiment, the lower (156) and upper (160) floors of the lower (152) and upper (154) baskets are porous to allow an activation solution 160 to flow therethrough when the pump is activated, which is explained in greater detail below.

In this embodiment, a volume of activation solution 166 occupies the void space defined by the upper basket 154, and a plug layer 145 occupies the void space defined by the lower basket 152. The plug layer 145 can keep the activation solution 166 from flowing through the upper floor 160 until the pump is activated. The plug layer 145 can be any material, or a plurality of materials, or a composition, including materials dispersed in suspension media such as gels and the like, that is (are) capable of contracting or expanding in size in response to an environmental stimulus. Examples of environmental stimulus for this and other embodiments include, without limitation: changes in temperature, pH, pressure, e.g., atmospheric pressure, salinity, ionic strength, exposure to selected light frequencies, selected acoustic wave frequencies, magnetic fields, vibration, or other environmental factors. In one embodiment, magnetic nanoparticles can be incorporated into the plug layer 145; application of pulsed magnetic fields can cause rapid movement of the nanoparticles which can result in localized heating so as to increase the temperature of the plug layer 145.

In one example, the plug layer 145 can prevent the solution 166 from entering the lower basket 152 by substantially plugging the pores of the upper basket floor 160 under a first environmental condition (such as a first temperature). Under a second environmental condition, (e.g., a second temperature), one or more constituents of the plug layer 145, e.g., SPH's within the plug layer 145, can contract to allow the solution 166 to drain from the upper basket 154 into the lower basket 152.

In one embodiment, the pump 100 can be activated when an environmental stimulus causes the solution 166 to drain from the upper basket 154, flow through the lower basket 152, and contact the polymer layer 140 to cause expansion of the polymer layer 140. As described herein, expansion of the polymer layer 140 into the conical-shaped void in the lower pump body 105 can cause the dispensable fluid 120 to be expelled from the pump 100, e.g., through the hollow passage 115. In general, the activation solution 166 can be chosen according to user preference or for a particular purpose; however, in a preferred embodiment, the activation solution 166 can be chosen to be maximally absorbed by the polymer layer 140. In one non-limiting example, the activation solution 166 is an aqueous solution. Suitable aqueous solutions include, but are not limited to: deionized water, saline solutions, e.g., 0.9% saline weight by volume, distilled water; or distilled water mixed with a chosen proportion of ethylene glycol. In another non-limiting example, the activation solution 166 is a solution composed of, or containing isopropyl alcohol or silicone oil.

In general, the activation solution 166 can be chosen based on desired operational characteristics and other functional considerations of the pump 100, as physical properties of the activation fluid can affect the operation of the pump 100. For example, the viscosity and density of the activation fluid can affect pump activation response time and other variables, which can be advantageous when designing a pump for a particular purpose. Generally, the dispensing action, e.g., the output flow rate of the pump can be controlled according to the rate at which the plug layer 145 contracts to allow the activation solution 166 to flow therethrough, the rate at which the polymer layer 140 absorbs the activation solution 166, or a combination thereof; however, other factors may also be applicable.

For example, isopropyl alcohol, when used as the activation solution, can be rapidly absorbed into a polymer layer 140 that includes a superporous hydrogel composite (SPHC). In such an example, the SPHC can include a filler agent that contains swellable particles that allow or enhance polymerization and crosslinking of the polymer simultaneously. Exemplary filler agents include, but are not limited to: sodium carboxymethylcellulose (Ac-Di-Sol), cross-linked sodium starch glycolate (e.g., Primojel™ provided by DFE Pharma) and cross-linked polyvinyl pyrrolidone (e.g., polyvinylpolypyrrolidone (Crospovidone)). The use of isopropyl alcohol as the activation solution 166 with a SPHC polymer layer 140 can lead to rapid dispensing of the fluid 120 (under 1 minute, in some embodiments). In a contrasting example, saline solutions are absorbed more slowly in a SPHC polymer layer 140, which can result in a relatively slower dispensing of the fluid 120. In yet another example, tap water (obtained from a municipal supply from Eden Medical headquarters, Howard Lake, Minn., U.S.A.) was found to cause the most rapid swelling of a SPHC polymer layer 140, leading to the fasted dispensing rate of the fluid 120 and the highest pump output pressure (immediate, after activation, and sustained) of all aqueous solutions tested.

In general, the plug material 145 can be chosen according to preference from materials known in the arts. In one non-limiting example, the plug material is an array of hydrogel beads in sufficient number, e.g., collective volume, to prevent the activation solution 166 from flowing through the upper basket floor 160 until the pump is purposefully activated, which is described in greater detail below. The pore size of the lower (156) and upper (160) floors can be chosen in consideration of the average individual size of the hydrogel beads, so as to reduce the likelihood of the pores becoming plugged by the beads. In a preferred embodiment, the size of the hydrogel beads can be selectively increased or decreased through the control of temperature or other environmental variables. For example, at least one type of thermoresponsive hydrogel bead decreases in size when heated. In other embodiments, hydrogels, including hydrogel beads can be used that undergo a change in size in response to one or more environmental stimuli.

In one embodiment, an environmental stimulus can include causing the collection of hydrogel beads to vibrate with sufficient energy to cause localized frictional heating. This heating can cause the hydrogel bead plug layer to contract or swell in size, depending on the type of hydrogel bead used.

In yet another embodiment, environmental stimulus can include exposing the plug layer to radiation, e.g., electromagnetic radiation. For example, light-sensitive hydrogel beads can be caused to contract or swell in size upon exposure to certain wavelengths of light. Thus, in one pump embodiment, the plug material 145 can include such light-sensitive hydrogel beads, and the pump can be activated by exposing the beads to the proper wavelength of light.

In some pump embodiments, environmental stimulus can be imparted to the plug layer via an input port disposed on the pump body where the plug layer is accessible by, e.g., catheter, syringe, or other device. For example, a pump can be activated by introducing a solution having a certain pH that causes a plug layer 145 to swell or contract according to pH-sensitive hydrogel beads contained therein.

One non-limiting example of a thermoresponsive hydrogel is one composed of N-isopropylacrylamide (NIPAAm). NIPAAm hydrogel beads can be synthesized with low or high initiator and accelerator concentration. One exemplary synthetic sequence for producing NIPAAm hydrogels includes combining 6 mL of N-isopropyl acrylamide (NIPAAm), 6 mL of acrylic acid, 6 mL of N—N'-methylene bisacrylamide (as the cross-linking agent) 1 mL of ammonium persulfate, and 100 μL, of tetramethylenediamine. In general, the swelling of NIPAAm hydrogel beads can be relatively fast, compared to other hydrogel bead variants, where the kinetics of the swelling can be controlled in part by varying the density of the cross-linking agent in the material. A process for synthesizing thermosensitive poly (N-isopropylacrylamide) hydrogel beads can be found in "Preparation of poly(N-isopropylacrylamide) hydrogel beads by circulation polymerization," H. Tokuyama and N. Yazaki, Reactive and Functional Polymers," 70(12), December 2010, pp 967-971.

Still referring to FIGS. 1A and 1B, in this embodiment, the pump 100 further includes a gasket 167 which can be sealingly engaged to the upper pump body 150, thereby forming a lid capable of retaining the activation solution 166 in the upper basket 154 together with the plug material 145. The gasket includes apertures 168a, 168b configured and positioned so as to overlap with bores 164a, 164b of the upper pump housing 150 when sealingly engaged thereto.

In this embodiment, the pump 100 further includes a cover 175. The cover 175 can be configured to be positionable atop the gasket 167 to provide sealing engagement of the gasket 167 to the upper pump housing 150 through, e.g., applied pressure. The cover 175 includes bores 177a, 177b configured and positioned so as to overlap with apertures 168a, 168b of the gasket 167 when sealingly engaged thereto.

In this embodiment, the bores and apertures of the various pump components, e.g., bores 117a-b of the lower pump body 105, apertures 129a-b of the flange 125, bores 164a-b of the upper pump body 150, apertures 168a-b of the gasket 167, and bores 177a-b of the cover 175 are aligned so that a fastener 180 or fastening mechanism extending from the lower pump body 105 to the cover 175 can be received therethrough, to include the other aforementioned components. Exemplary fasteners include, but are not limited to: bolts, clamps, couplings, dowels, hooks, latches, lugs, nails, pins, rivets, including pop rivets, and screws. FIG. 1A includes a fastener 180, in this example, a dowel, extending from the lower pump body 105 for illustrative purposes. Components of the pump 100 can be fastened together using glues, cements, resins, or other compounds known in the art in lieu of, or in addition to the use of the aforementioned fastening mechanisms.

Certain pump components that provide mechanical strength or support of the pump 100, e.g., the lower pump body 105, flange 125, upper pump body 150, and cover 175 can be composed of bio-compatible polymers, metals, ceramics or other materials according to preference and the indented use of the pump 100. One non-limiting example of a bio-compatible polymer that can be used in this and other embodiments is sold under the MED610 brand, offered by Objet Inc., of Billerica, Mass., USA. In some embodiments, consideration can be given to the thermosensitive or pH-sensitive nature of hydrogel beads, if they are used as a plug material, and the choice of material for the aforementioned pump components can be selected so as to have a desired amount of thermal conductivity.

Figure 2A:
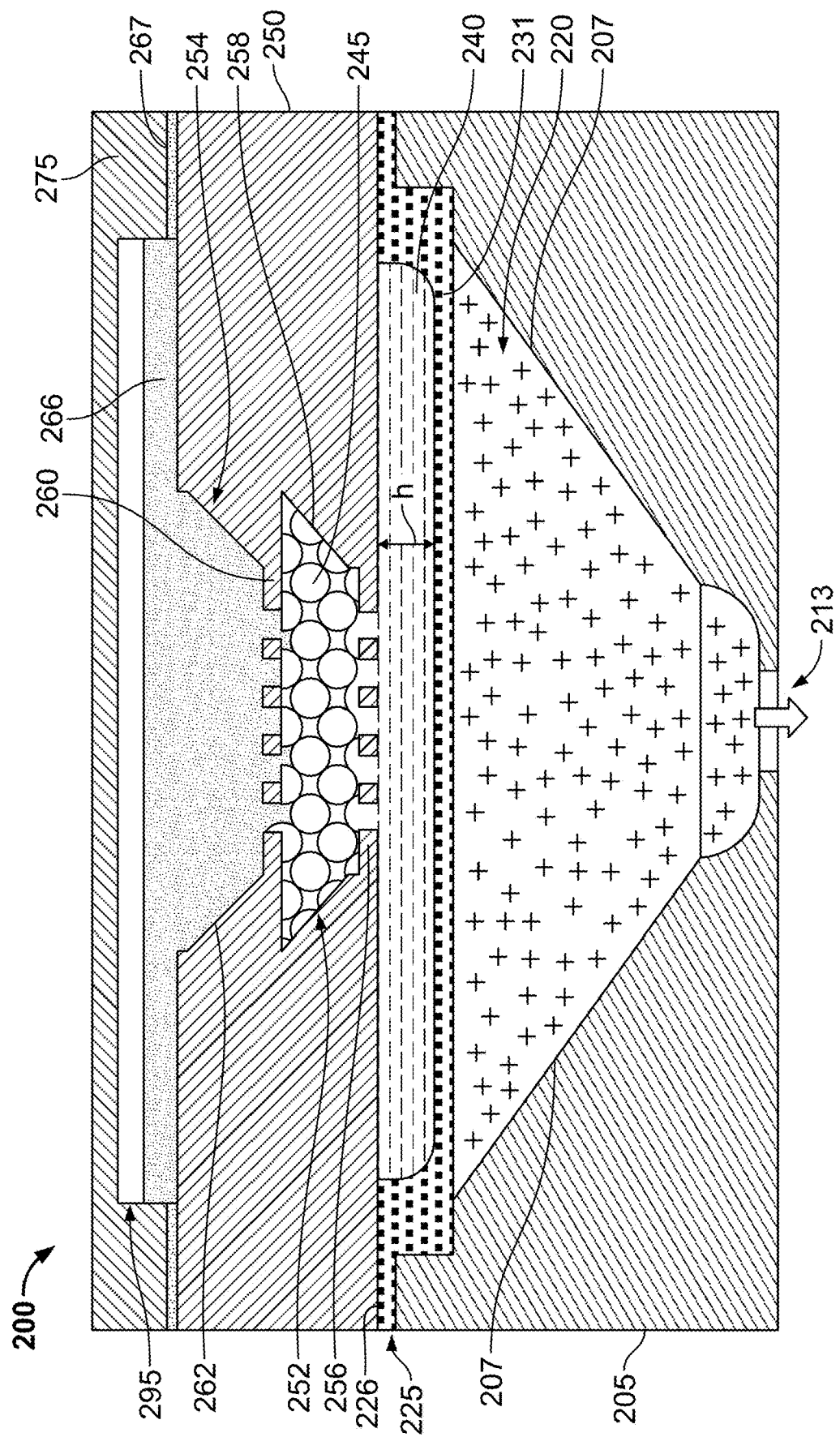
FIG. 2A is a cross-sectional view of a pump in a pre-activated configuration, according to one embodiment.
Figure 2B:
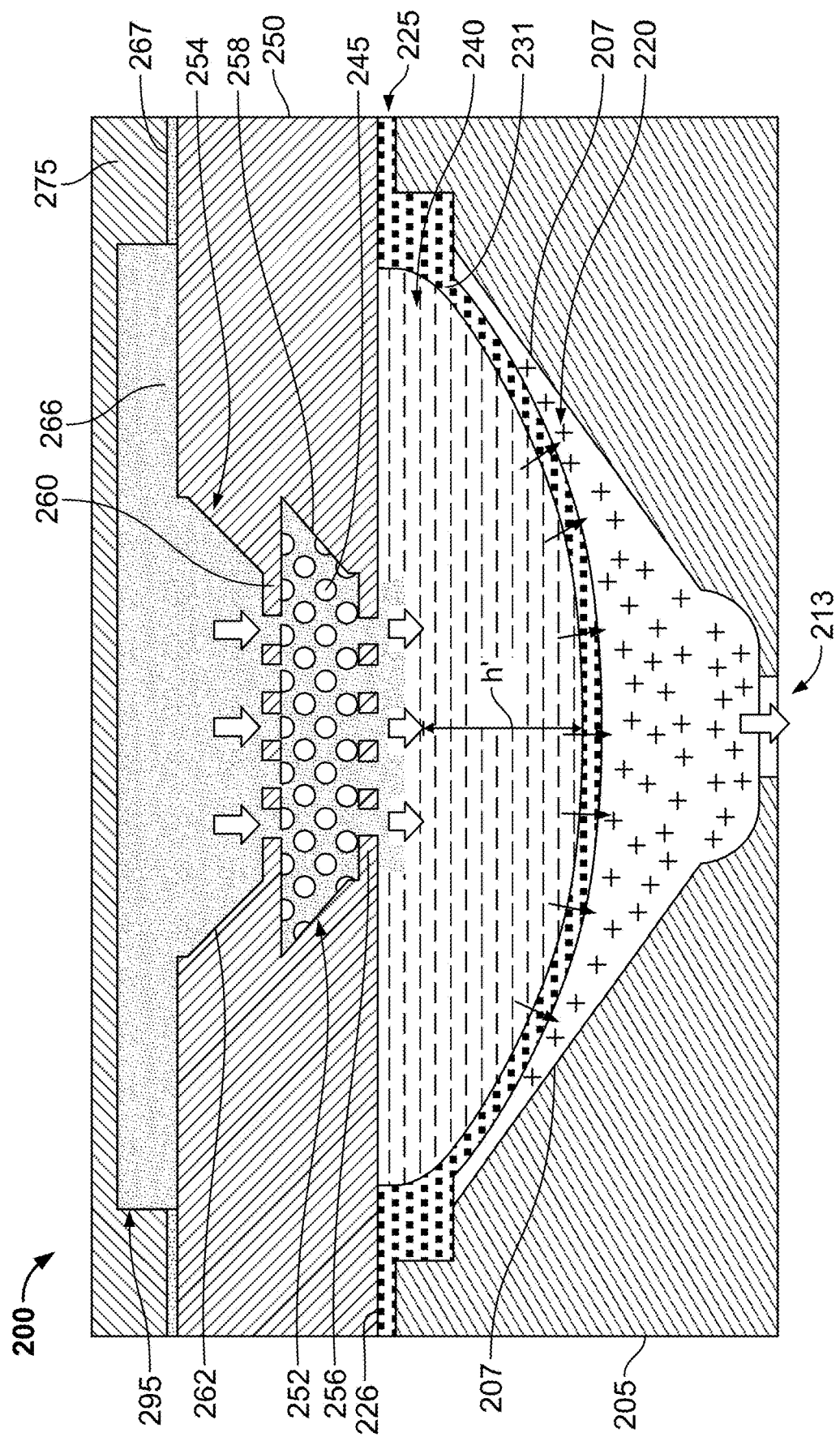
FIG. 2B is a cross-sectional view of a pump in an activated configuration, according to one embodiment.

Referring now to FIGS. 2A and 2B, a pump 200 is shown according to one embodiment. In this embodiment, the pump 200 includes a lower pump body 205 having a conical-shaped cavity defined in part by inner wall 207 for holding a volume of dispensable liquid 220. The liquid can be forced out of the lower pump body 205 via an exit port 213 in a manner described in greater detail herein. The exit port can be plugged with a suitable material, or, alternatively, the plug can include a one-way valve or suitable alternative device to prevent the dispensable liquid 220 from exiting the lower pump body 205 prior to activation of the pump 200. In some embodiments, the exit port 213 can include one or more attachment mechanisms for securely receiving a lumen, tube, or other liquid 220 transporting material so that the dispensable liquid 220 can be delivered to a chosen location when the pump is activated. In some embodiments, the exit port 213 can be a threaded bore configured to receive a corresponding threaded lumen which can be reversibly attached for the purpose of transporting fluid 220 from the lower pump body 205 to a chosen location. In some embodiments, the exit port can be configured to interlock with a device, such as a medical device, which can be configured to receive the fluid 220 for a particular purpose. In one example, the fluid can be an adhesive sealant compound, and the device can be a member of a continent ostomy wafer capable of sealing with, or reversibly sealing with a patient's skin.

In this embodiment, the pump 200 includes a flange member 225 sealingly engaged with the lower pump body 205 and serves, in part, to retain the dispensable fluid 220 within the lower pump body 205 until the pump 200 is activated. The flange member 225 includes a resiliently flexible diaphragm 231 that is capable of being flexed from a first conformation to a second conformation. For example, in this embodiment, the first conformation can be the conformation shown in FIG. 2A, where the diaphragm is substantially flat, and not flexed in the +/−z-direction, which can be a pre-pump activation configuration; the second conformation can be the conformation of the diaphragm shown in FIG. 2B, where the diaphragm is outwardly flexed from its circular midpoint from the first conformation and extends into the conical-shaped cavity of the lower pump body 205 (in the −z direction). The latter conformation, or any conformation where all or part of the diaphragm is stretched or displaced from its equilibrium position, e.g., the first conformation, can be the activated pump conformation.

In this embodiment, the diaphragm 231 is recessed from the top wall 226 of the flange, thereby defining a disk-shaped cavity of height h for storing a layer of expandable material 240 as shown in the pre-pump activation conformation of FIG. 2A. When the pump is activated (described in further detail below) the expandable material 240 can expand, thereby urging all or part of the diaphragm 231 into the conical-shaped cavity of the lower pump body 205 (FIG. 2B). In this and other embodiments, the expandable material layer 240 can be a polymer capable of absorbing a fluid to increase its volume from a first volume to a second, larger volume. In some embodiments, the polymer can be capable of absorbing fluid to increase the volume of the expandable material 240 from a first volume to a second, larger volume, and subsequently releasing fluid to return to approximately the first volume. Exemplary polymers for this purpose include, without limitation, the class of polymers generally known as superporous hydrogels (SPH's) described above.

In this embodiment, an upper pump body 250 is sealingly engaged with the flange member 225 as shown in FIGS. 2A and 2B. The upper pump body 250 includes a lower reservoir 252 which, in this embodiment, has the general shape of an inverted truncated square pyramid as defined by an inner reservoir wall 252. In this embodiment, the lower reservoir 252 includes a porous floor 256 capable of allowing passage of a volume of activation solution 266 therethrough when the pump is activated. In this embodiment, the upper pump body 250 also includes an upper reservoir 254, also having a general shape of an inverted truncated square pyramid as defined by inner reservoir wall 262, for storage of the solution 266. The upper (254) and lower (252) reservoirs are divided by a porous floor 260 configured to allow fluid communication therebetween, as illustrated in FIGS. 2A and 2B.

In this embodiment, the lower reservoir 252 contains a volume of hydrogel beads 245. In this and other embodiments, the hydrogel beads 245 can be size-dependent according to factors (variables) of the surrounding environment, as previously described. In several non-limiting examples, the size, e.g., the mean diameter of the individual hydrogel beads can change according to surrounding temperature, the pH, or ionic strength of the activation solution 266, or other factors. As described herein, thermosensitive hydrogel beads 245 are capable of shrinking or expanding in volume according to temperature. Suitable hydrogel beads 245 include those hydrogel beads described herein and equivalents known in the art. The individual size of the hydrogel beads 245 can be chosen to maximize performance of the pump 200 (as described below) and also in consideration of the pore sizes of the porous floors 256 and 260, so as not to plug the individual pores thereof.

In this embodiment, a pump cover 275 sealingly engages a gasket 267 which serves, in part, to retain the activation solution 266 within the upper reservoir 254 and the void space defined in part by pump cover inner wall 295. The dashed line 290 in FIG. 2A serves to illustrate the base of the inverted truncated square pyramid shape of the upper reservoir 254 and is not a structural component of the pump 200. While not shown in FIG. 2A or 2B, in this and other embodiments, including the embodiments shown in FIGS. 1A and 1B, the pump cover can include sealable ports for introducing (drawing out) activation solution 266 into (from) the upper reservoir 254 and the void space defined in part by pump cover inner wall 295. Such structure provides the capability to replenish the activation solution 266 if needed, such as after an activation of the pump 200.

Figure 2C:
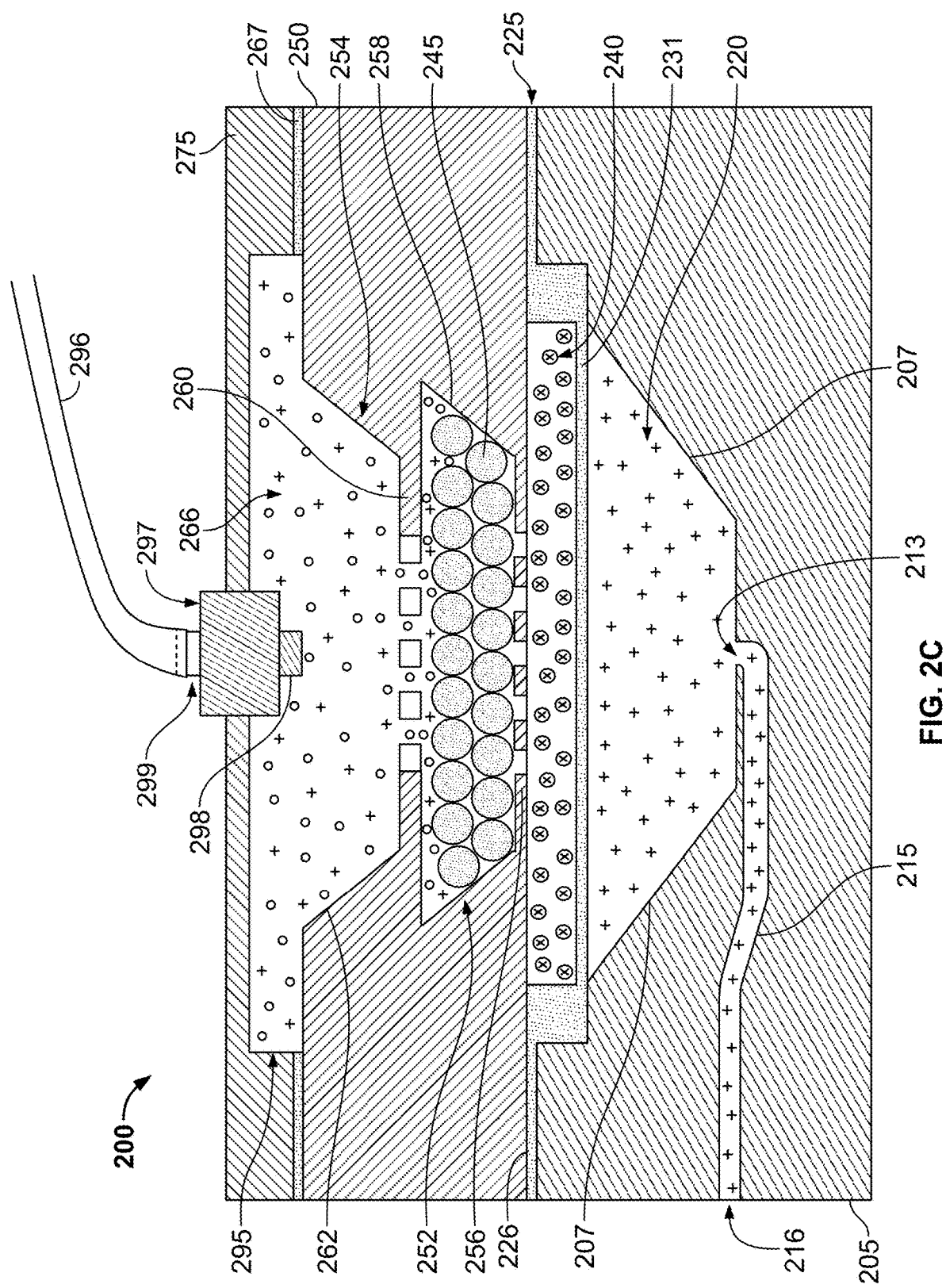
FIG. 2C is a cross-sectional view of a pump in a pre-activated configuration, according to one embodiment.

Referring now to FIG. 2C, in this and other embodiments, pumps of the type described herein can include access ports for delivering fluids, gasses, or other materials into the upper reservoir 254 for activating the pump, or replenishing the activation fluid 266 of the pump 200. The pump 200 shown in FIG. 2C can contain the same structural elements as that described with respect to FIGS. 2A and 2B; in addition, in this embodiment, the pump 200 includes a valve housing 297 configured to sealingly engage with the pump cover 275. In this embodiment, the valve housing 297 houses a one-way valve within the housing (not shown in FIG. 2C for clarity) that allows fluids or gasses to flow into the upper reservoir 254, but restricts flow in the opposite direction. It will be understood that a one-way valve is one of many valve alternatives that can be used to achieve the same or similar functionality in other pump embodiments. In this embodiment, the valve housing 297 further includes a fitting 299 for coupling a terminal end of a lumen 296 to the housing 297. Suitable couplings include, but are not limited to: nipples, plugs, Luer connectors, and plungers. In other embodiments, the fitting 299 can allow a user to inject a solution into the upper reservoir 254 using, e.g., a syringe or similar device. In such cases, the fitting 299 can be a rubber seal or cap. In this embodiment, an output port 298 of the valve housing allows liquids or gasses received via the lumen 296 to enter the upper reservoir 254.

The embodiment of FIG. 2C is one of many examples that can allow a user to activate the pump 200 by administering a liquid or gas into the upper reservoir 254. In such cases, the injected liquid or gas can be one which causes the plug layer, in this case, the hydrogel beads 245 to contract in size, thereby allowing the activation liquid 266 to flow through the porous floors 256, 260, and reach the expandable material layer 240. In another embodiment, the pump can be activated without environmental stimulus by administering a liquid or gas into an empty upper reservoir 254 (e.g., absent hydrogel beads 245). In this embodiment, the introduction of liquid or gas can directly contact the superporous polymer to immediately invoke expansion of the diaphragm 231 into the conical-shaped void and cause corresponding pump operation.

In one embodiment, the hydrogel beads 245 can have a size dependence based on the pH of a surrounding liquid medium. In such an embodiment, the pH of the activation fluid 266 can be changed to activate the pump. For example, at a first activation fluid 266 pH, the hydrogel beads 245 can retain a certain size that substantially precludes the activation fluid from flowing through the porous floors 256, 260; however, at a second activation fluid 266 pH, the hydrogel beads 245 can contract in size, thereby allowing the activation fluid 266 to flow through the porous floors 256, 260 and contact the expandable material layer 240 to activate the pump 200.

In one embodiment, the rate that the activation fluid 266 is exposed to the expandable material layer 240 can be controlled by regulating factors of the environment immediately surrounding the hydrogel beads 245. In one example, consider that the layer of hydrogel beads 245 will contract to a minimum size when the pH of a fluid surrounding the individual beads is 4.0, and that the pump 200 is stored in a non-activated configuration wherein the activation fluid is an aqueous solution having a pH of 7.0. In this example, introducing a highly acidic solution can cause a rapid pH change in, and around the hydrogel beads 245, causing a rapid contraction in size, and a rapid dumping of the activation fluid 266 onto the expandable material layer. In this example, the pump 200 can be expected to rapidly expel the dispensable fluid 220 from the pump 200. However, the rate of pH change can be governed so that the contraction of the hydrogel beads 245 is gradual, instead of rapid, which can lead to a slower activation of the pump 200 and a slower expulsion of the dispensable fluid 220. In one example, a less-acidic solution e.g., a solution of pH 5.0 can be introduced into the upper reservoir 254 to slow the activation of the pump.

In general, components of the pump embodiments described herein can be fabricated from bio-compatible materials. For example, referring back to FIG. 1A, the lower pump body 105, upper pump body 150, cover 175, and any other component can be formed from a bio-compatible plastic so that the pump can be implanted into a human or animal subject. In another example, referring to FIG. 2C in particular, the pump 200 can be formed from a bio-compatible plastic so as to be implantable as just described, wherein the valve housing 297 can be a portal that protrudes out of the skin or other tissue to allow administration of fluids or gasses into the upper reservoir 254 by a physician or other user.

In general, pumps of the types described herein can be activated using various methods. The choice of method used can depend on material properties of the pump or pump components, in particular, the material properties of hydrogel beads, if incorporated, the intended use of the pump, and other considerations that will be apparent to those skilled in the relevant arts. Reference is made in the following description to components of the pump 200 in FIGS. 2A and 2B, however, it will be understood that the terms and description are equally applicable to other pump embodiments, equivalents, and alternatives, including the embodiment of FIGS. 1A and 1B. As described herein, "activating" the pump 200 refers to one or more steps that result in the dispensable liquid 220 stored in the lower pump body 205 being dispensed from the pump 200 via the exit port 213 (or, in the embodiment of FIGS. 1A and 1B, being dispensed through the aperture 113 of the floor 111, and through the hollow passage 115).

One particular advantage of the concepts provided herein is that the disclosed pumps can be activated without requiring an external power source, such as commercial, residential, or battery-supplied electricity. Although any of the disclosed embodiments can be adapted to use electrical power if desired, in general, the environmental changes that can cause the plug layer or the hydrogel bead layer to contract to activate the pump can be engendered without an external power source.

In general, the operational characteristics of a pump of the type described herein can be dependent on material factors of the pump constituents. Certain uses of a pump may call for rapid expulsion of the dispensable liquid 220, while other uses may benefit from a slow, steady flow of the dispensable liquid 220. The expulsion rate of the dispensable liquid 220 can be dependent on, among other factors, the cross-sectional area the diaphragm, exit port outlet pressure (if regulated by a plug, valve, or other flow-restriction mechanism), and the cross-sectional area of the pump exit port. In general, the maximum operating pressure of a pump of the type described herein can be determined by the force per unit area across the pump diaphragm, which is largely dependent on the expansion rate and volume capacity of the polymer layer adjacent thereto. The amount of fluid absorbed by the polymer can be controlled by the valve action, e.g., the dynamics of the plug layer as it is exposed to environmental stimuli. The pump output flow rate of the dispensable fluid can be affected by the flexibility and pliability of the diaphragm, and the material properties of the fluid, gas or gel, e.g., density, compressibility, volumetric flow rate, etc. The flexibility of the diaphragm can generally be selected by considering the geometry of the diaphragm, e.g., its thickness, the mechanical properties of the diaphragm and the geometry of the fluid-retaining chamber. The elastic modulus and Poisson's ratio are mechanical diaphragm properties that can be considered when designing a pump of the type described herein for a particular use.

In one embodiment, a pump of the type described herein can be thermally activated, e.g., activated by changing the temperature of the pump or one or more of its components. In particular, a pump can be activated by engendering a temperature change to the plug material, e.g., plug material 145 described with respect to FIGS. 1A and 1B, the collection of thermoresponsive hydrogel beads 245 described in FIGS. 2A and 2B, or variants and equivalents thereof. In another embodiment where the plug material of the pump includes pH-sensitive hydrogel beads, the pump can be activated by exposing the hydrogel beads to a solution having a pH that causes the size of the beads to shrink, e.g., by introducing the solution into the upper basket 254 of the upper pump housing 250. In such an embodiment, the pump cover 175 can include an input port capable of receiving fluids from a syringe, catheter tube, or other source. The solution can be introduced manually, or, in some embodiments, as part of a bio-feedback system that monitors an aspect of a patient's physiology and causes the solution to be injected into the pump when certain pre-established criteria are met. In one example, an aspect of a patient's physiology can be a blood sugar concentration, and the solution can be insulin.

In another example, referring to FIG. 2A, the pump 200 can include a plurality of substantially spherical, thermoresponsive hydrogel beads 245 which, at a first temperature, are of an average size to adequately prevent the activation solution 266 from flowing through the porous floor 260 of the upper reservoir 254 into the lower reservoir 252. In one embodiment, the hydrogel beads 245 can have an average diameter that is at least twice the diameter of the pores of the porous floors 260 and 256, assuming substantially equal pore size in both floors.

As described herein, and as known in the art, some thermoresponsive hydrogels are capable of shrinking in average size when heated. Thus, activation of the pump can include engendering a temperature change to the collection of hydrogel beads 245 to cause them to shrink to a size that allows the activation solution 266 to flow from the upper reservoir 254 to the lower reservoir 252, and through the floor (256) of the lower reservoir.

FIG. 2B illustrates the pump 200 in an activated state, where a temperature change has caused the hydrogel beads 245 to shrink in size, which has caused the activation solution 266 to be released from the upper pump body 250 unto the expandable material 240. As previously described, the expandable material 240 can be one which is capable of absorbing all or some of the activation solution 266 which can cause a substantially concurrent increase in volume, as previously described. Comparing the illustrated volume of the expandable material 240 in FIGS. 2A and 2B, it can be seen that the absorption of the solution 266 causes significant swelling of the expandable material 240 when the pump is activated. The swelling of the material 240 creates outward expansion force in all directions; however, the upper pump body 250 can be composed of a rigid or semi-rigid material such as PMMA that resists the expansion force and urges the material and the diaphragm 231 into the conical-shaped cavity of the lower pump body 205 as illustrated in FIG. 2B. In this embodiment, the expansion force of the expandable material 240 urges the dispensable fluid 220 to the exit port 213, where it can be channeled or flowed to a desired location as explained herein.

In general, a pump of the type described herein can be activated in accordance with the above description by various methods. In one non-limiting example, a pump can be activated through application of a heat source to the body of the pump. The solid components of a pump, e.g., the lower pump body 205, upper pump body 250, and pump cover 275 can be formed from a material having a desired amount of thermal conductivity. In some cases, it can be beneficial to form the solid components from a material having a high thermal conductivity, e.g., in situations where the desired reaction time of pump activation is relatively fast. In other cases, however, it can be beneficial to form the solid components from a material having a lower degree of thermal conductivity, so that accidental or unintended activation of the pump is not caused by ambient temperature fluctuations.

In general, a pump of the type described herein can be configured to protect the inner components and cavities (e.g., the conical-shaped cavity of the lower pump housing 205, diaphragm 231, lower (252) and upper (254) reservoirs, expandable material 240, and hydrogel beads 245) from outside sources of moisture or other fluids. In other words, the pump can be substantially impervious to water and other fluids.

In general, the rate at which the dispensable fluid is dispensed from pumps of the type described herein can be controlled according to one or more material considerations. In a first material consideration, the plug layer material (145, FIGS. 1A and 1B) or the hydrogel beads (245, FIGS. 2A and 2B) can be chosen for their degree of thermoresponsiveness. Without wishing to be bound by theory, it is presumed that materials having a higher degree of thermoresponsiveness will generally respond more quickly to temperature changes of the ambient surroundings and vice-versa. In another consideration, the material and mechanical characteristics of the diaphragm can affect the expansion rate of the expandable polymer layer (e.g., polymer layer 140). In general, with all other factors equal, a thinner diaphragm can be urged into the conical-shaped cavity of the lower pump body 105 by the expandable polymer (when activated) faster than a diaphragm having a relatively greater thickness. In general, a diaphragm having a higher degree of elasticity can provide the flexibility to exert higher output compression forces. Additionally, the diaphragm can be formulated from rubber or other compounds having a desired degree of elasticity for a particular purpose or application.

In general, any type of SPH can be incorporated as, or in the plug layer 145 or the thermosensitive hydrogel beads 245 as described above with respect to FIGS. 1A-2B for actuating the pump. In one approach, a SPH polymer with additional monomer, e.g., about 0.877% additional monomer can be used. In another approach, a superporous hydrogel with an interpenetrating polymer network (SPIH) can be used, which incorporates a second polymer network inside of an SPH to strengthen the polymer structure. SPIH hydrogels can have enhanced mechanical properties compared with SPHs, including higher compression strength and elasticity, making them a potential candidate for use as a pump actuator. The enhanced properties may be attributable to scaffold-like fiber network structures formed inside the cell walls of SPHs.

In general, the various components of a pump of the type described herein can be composed of various materials known in the art, the choice of which may depend on one or more considerations, including: cost, including manufacturing and raw material cost, disposability of the pump, operability, ruggedness, resistance to degradation from heat, radiation, chemicals, or aesthetic value.

In general, some pump applications—e.g., wound therapy applications—can benefit from a pulsed delivery of the dispensable fluid. In some embodiments, a pump of the type described herein is capable of producing a pulsed output, e.g., a controlled flow of the dispensable fluid for a certain period of time, followed by an "off" period, followed again by an "on" period of the controlled flow. Pulsed dispensable fluid output can be achieved, among other approaches, through application of periodic environmental stimulus to the plug layer, or by manually introducing pressure to one of the pump chambers, e.g., upper basket 154 or lower basket 152 using, e.g., a syringe to deliver gas or liquid as previously described.

In one embodiment, a pump of the type described herein can contain an activation solution within a burstable pouch or similar type of container. The activation solution can be in fluid communication with the plug layer, e.g., plug layer 145 when the pouch is broken, and the pouch can be caused to burst by force or other methods when desired by the user. Referring back to FIG. 1A, in one example, the pump 100 can include a burstable pouch of activation solution 166 positioned in the upper basket 154. The cover 175 and the gasket 167 can be flexible, so that a user can push down on the top of the pump 100 to cause the burstable pouch to burst, thereby releasing the activation solution, which can cause the pump to activate and release the dispensable fluid 120 as previously described. Such an embodiment can have particular advantages for remote use when access to environmental stimulus of the type described herein is unavailable, e.g., in military combat situations where soldiers may have limited resources.

In some pump embodiments, e.g., embodiments where the pump is configured for remote or body-worn use, the use of lab-on-a-chip technology can be incorporated into the pump design for sampling body fluids or other physiological measurements. In one such embodiment, the power source for the lab-on-a-chip assembly (not shown in FIGS. 1A-9) can be an air-bursting detonator. An air bursting detonator can supply energy by releasing stored gas when triggered by a short electrical pulse, as described, e.g., in "Disposable Smart Lab on a Chip for Point-of-Care Clinical Diagnostics," C. H. Ahn et al., Proc. IEEE Vol. 92 (1), January 2004, 154; and U.S. Pat. No. 7,524,464 entitled "Smart disposable plastic lab-on-a-chip for point-of-care testing" to Ahn et al., which is incorporated herein in its entirety by reference for all purposes.

In some pump embodiments, particularly those embodiments incorporating lab-on-a-chip technology as previously described, surface energy gradient dispensing methods can be used to improve flow properties of fluids. Such methods can be advantageous for reducing the energy required to transport fluids, enhance droplet formation, directing the movement of droplets, facilitate mixing of on-chip reagents or compositions, promoting sensory reactions, e.g., controlling the rate of diffusion in, e.g., glucose sensing, reducing variability in sampled fluid volumes and flows, etc. One exemplary surface energy gradient dispensing method is described in U.S. Pat. No. 7,790,265 to Brian Babcok, entitled "Surface-energy gradient on a fluid-impervious surface and method of its creation using a mixed monolayer film," which is incorporated in its entirety herein by reference for all purposes.

The following example is illustrative only; the materials and methods used in carrying out the experiments and the measured characteristics of the pump are in no way limiting with respect to the inventive concept or the claims.

A pump similar to that shown in FIGS. 1A and 1B was assembled and included: a lower pump body composed of PMMA, which included a conical-shaped chamber for storing a solution of a sealant fluid and an exit nozzle capable of discharging the sealant fluid when the pump was activated. A 100 kPa silicon pressure sensor (MPX 100, Motorola, Inc.) was used to measure pump exit pressure. A natural latex rubber diaphragm composed of a 270 μm thick elastic membrane sealed the sealant fluid within the conical-shaped chamber as previously described. A layer of NIPAAm expandable polymer having a weight of approximately 0.2 grams was applied to the top side of the diaphragm. An upper pump body was sealingly engaged to the flange; the upper pump body stored an aqueous activation solution that was released to the NIPAAm layer when the one-way valve was opened. The pump was activated using a one-way valve (Model No. F-2804-403, Pneuaire, Inc.) that was mounted in an upper pump body to simulate activation by hydrogel beads (245, FIGS. 2A-2B). The upper pump body was sealingly engaged to the flange. The assembled pump measured 16 mm×16 mm×14.8 mm, and had a fluid capacity of 3.0 mL.

Figure 3:
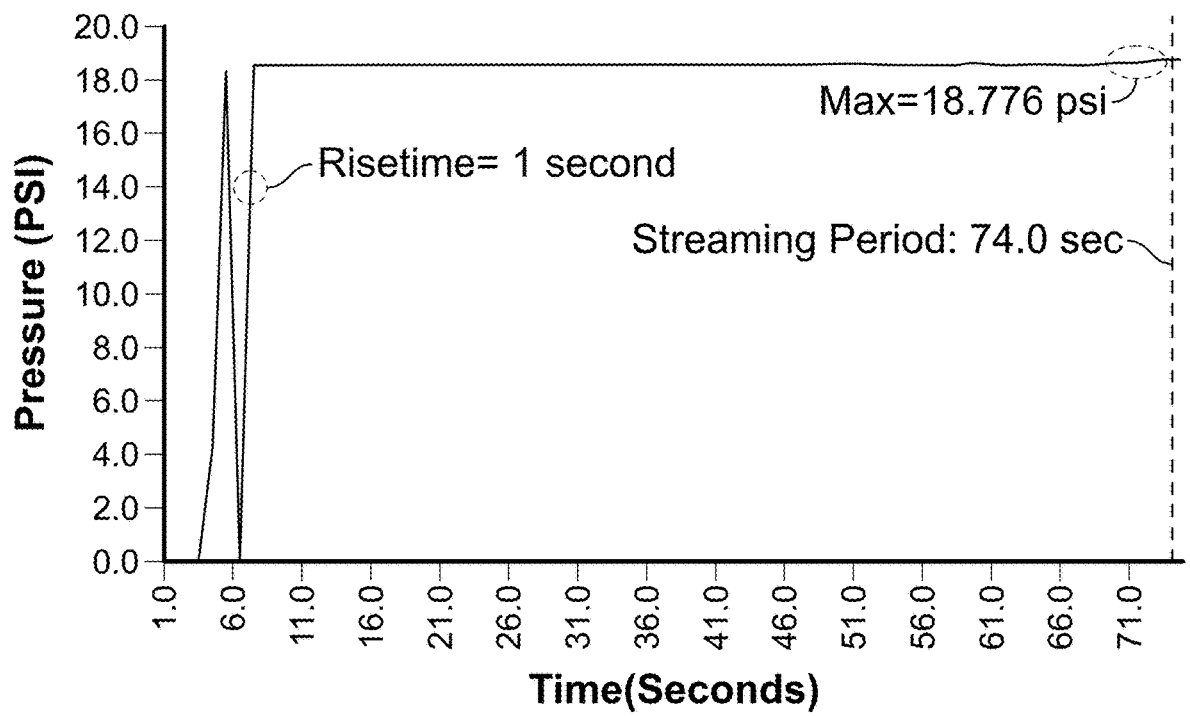
FIG. 3 is a chart showing measured pump output pressure versus time.

Referring now to FIG. 3, a graph showing measured pump pressure output vs. time is shown. The graph illustrates short-duration pump streaming characteristics, marked by a rapid pressure rise time of approximately one (1) second, and a holding pressure of approximately 18.776 psi for a period of at least 71 seconds.

Figure 4:
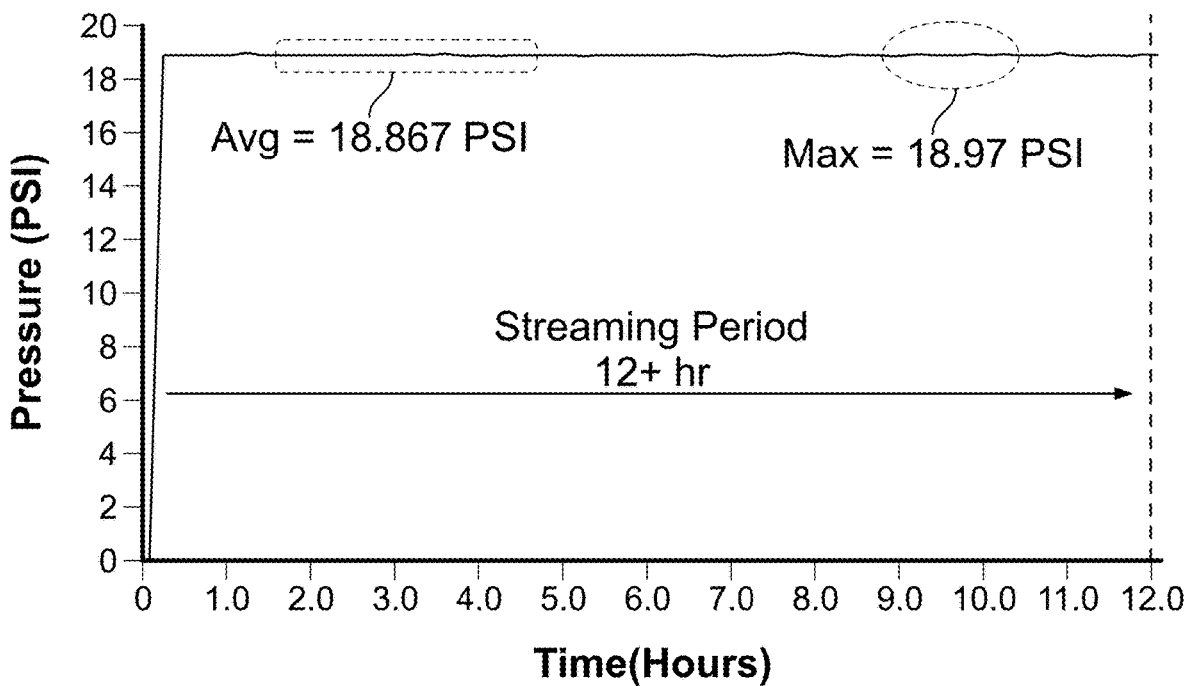
FIG. 4 is a chart showing measured pump output pressure versus time.

Referring now to FIG. 4, a graph showing measured pump pressure output vs. time is shown. The graph illustrates long-duration pump streaming characteristics, marked by a rapid pressure rise time of approximately one (1) second, and a holding pressure of approximately 18.867 psi for a period of greater than 60 hours.

Figure 5:
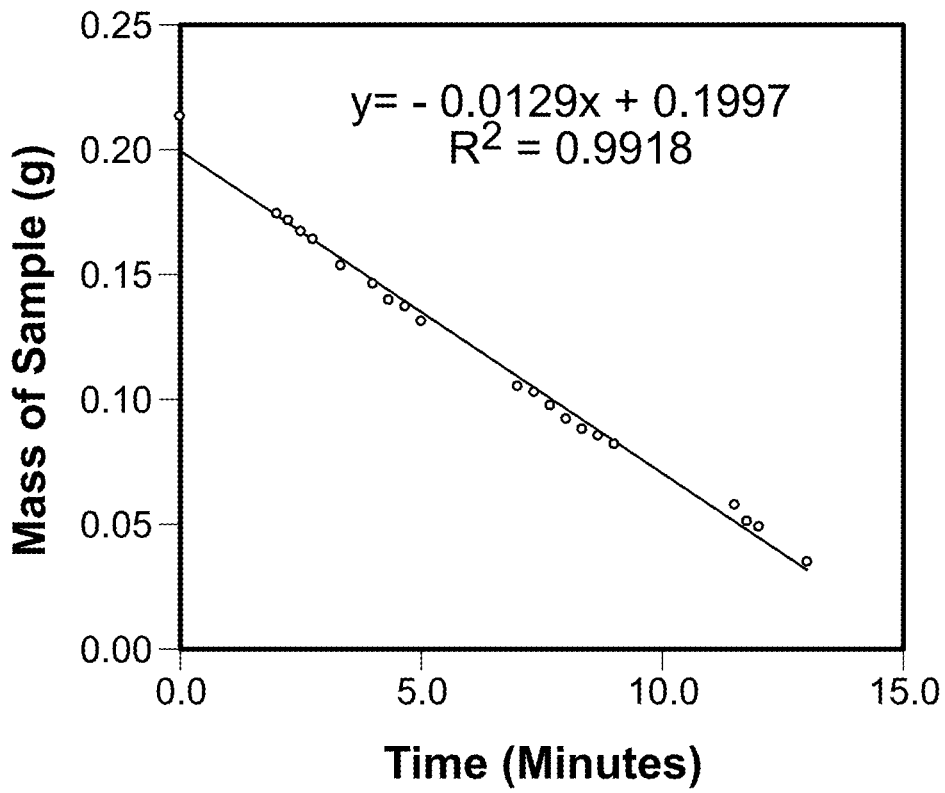
FIG. 5 is a chart showing sample mass versus time.
Figure 6:
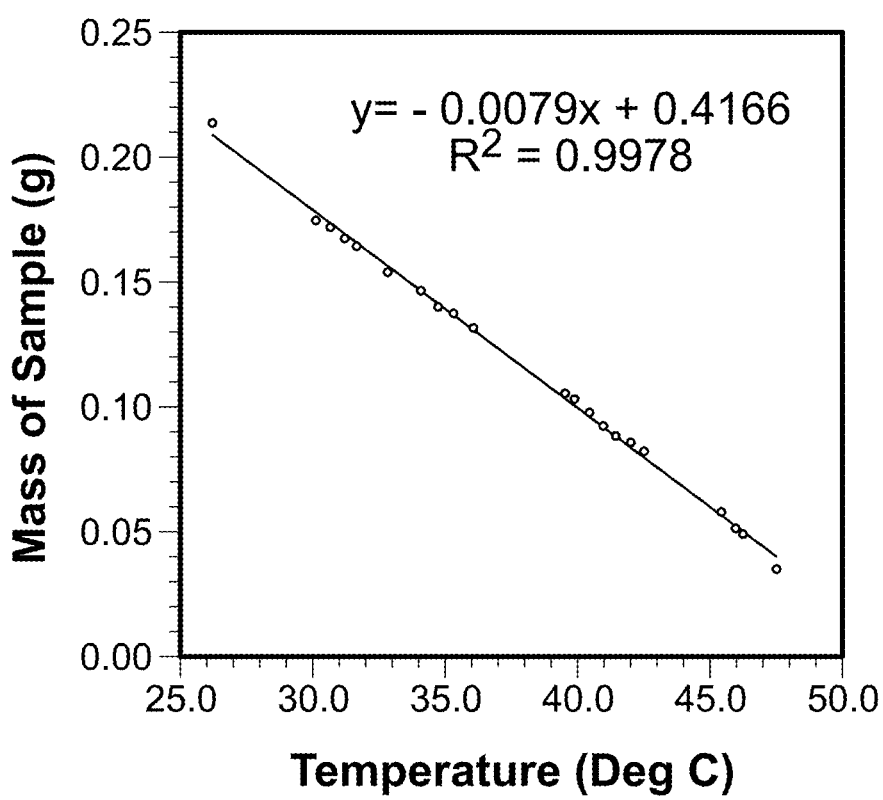
FIG. 6 is a chart showing sample mass versus temperature.

Referring now to FIGS. 5 and 6, the swelling kinetics of the NIPAAm hydrogel is shown. The charts illustrate the time- and temperature-dependent swelling characteristics of the NIPAAm hydrogel which can be used as a pump activator (e.g., the plug layer 145 in FIGS. 1A-1B, or the hydrogel beads 245 in FIGS. 2A-2B). The hydrogel was a clear gel synthesized by combining 6 mL of N-isopropyl acrylamide (NIPAAm), 6 mL of acrylic acid, 6 mL of N—N'-methylene bisacrylamide (a cross-linking agent), 1 mL of ammonium persulfate, and 100 μL of tetramethylenediamine. The kinetics of swelling (i.e. de-swelling for pump operation) of these hydrogels are relatively fast, capable of losing approximately 85% of water mass over a period of about 13 minutes and a concurrent temperature increase of approximately 21° C. The kinetics of the swelling or de-swelling can be controlled in part by varying the cross-linker density of the NIPAAm hydrogel.

As described above, a pump of the type described herein can be activated by a variety of environmental stimuli to the plug layer (e.g., plug layer 140 or the hydrogel beads 240 described above). In one pump embodiment, the pump can be activated by exposing the hydrogel beads to a solution having a pH that causes the beads to contract; the pump can be activated in a similar manner to those described above that are activated by thermo-sensitive hydrogel beads.

Figure 7:
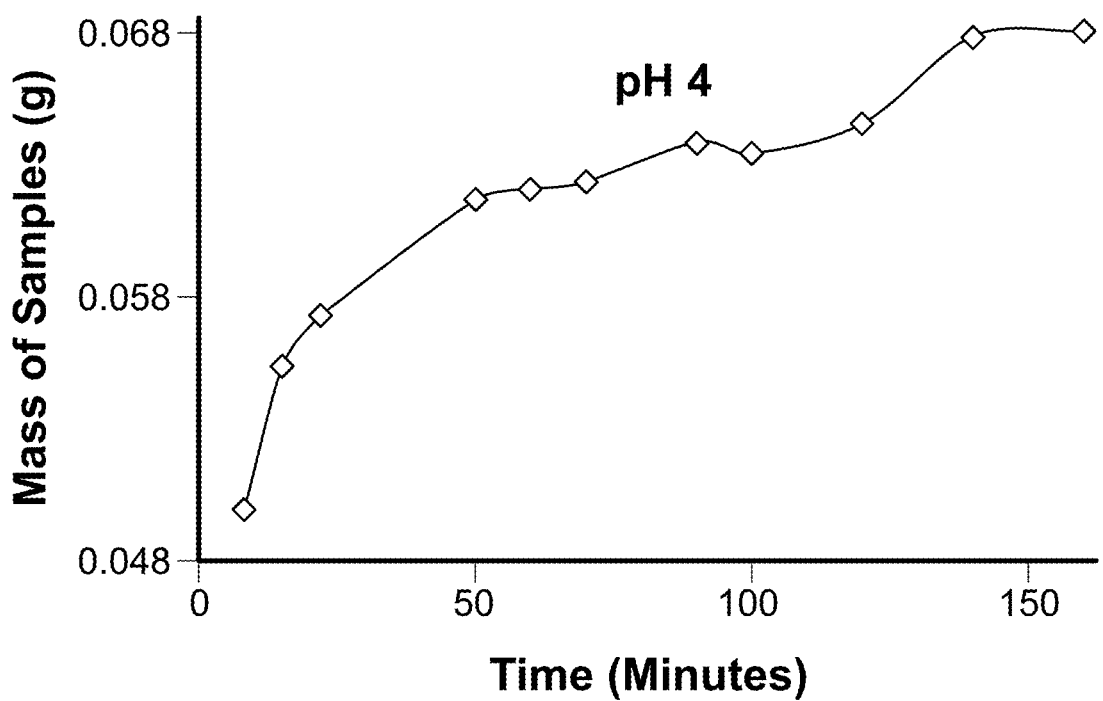
FIG. 7 is a chart showing sample mass versus time at pH 4.0.
Figure 8:
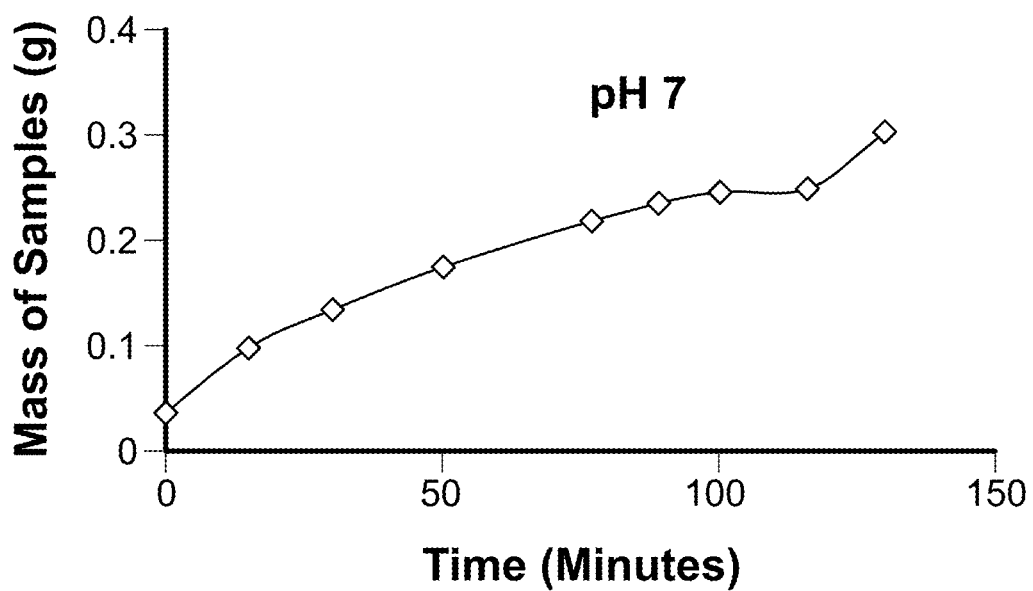
FIG. 8 is a chart showing sample mass versus time at pH 7.0.
Figure 9:
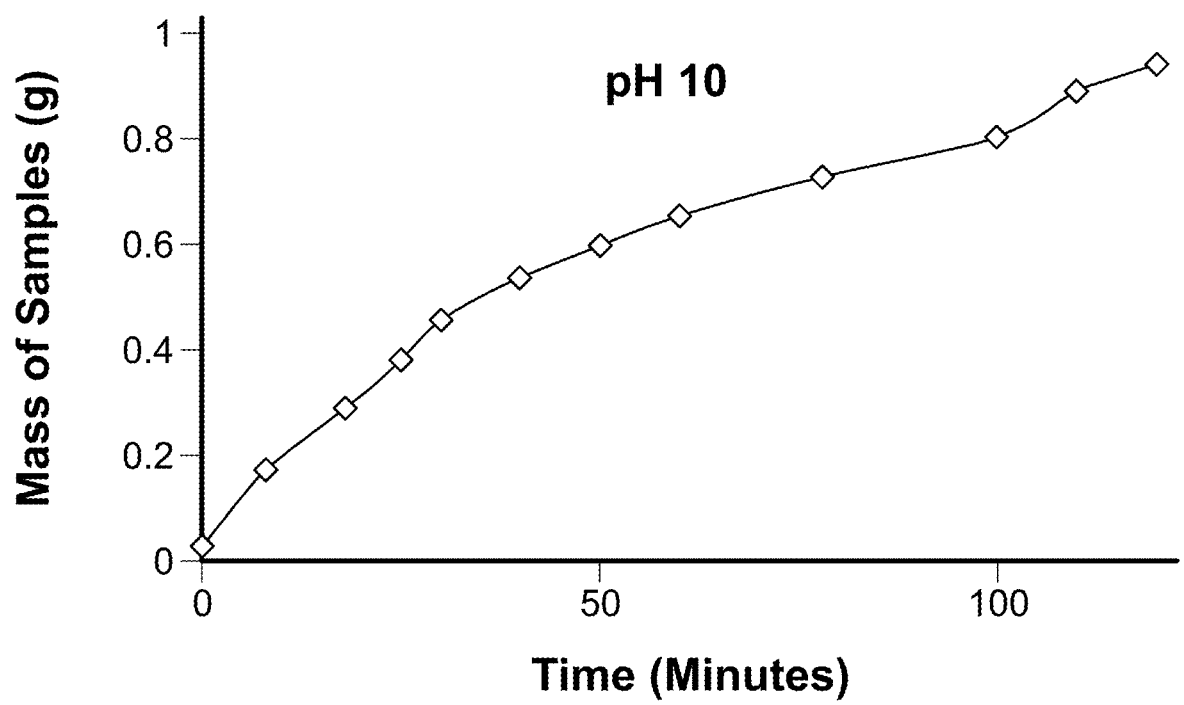
FIG. 9 is a chart showing sample mass versus time at pH 10.0.

Referring now to FIGS. 7, 8 and 9, swelling data for NIPAA copolymer hydrogels are shown. The extent and kinetics of NIPAA swelling appear to be pH-dependent, where, without wishing to be bound by theory the characteristics can be attributed to the presence of acrylic acid component in the hydrogel chain. The extent of swelling and the kinetics of swelling increases with pH over comparable period of time. The extent of volume swelling at pH 4, pH 7 and pH 10 after 100 minutes of equilibration of the dried co-polymeric NIPAA hydrogels in aqueous solution are 27%, 565% and 2407% respectively.

It should be understood that various modifications may be made to the miniature pumps described herein. For example, it may be advantageous in some circumstances to modify or adapt certain components for a particular use. Similarly, it may be advantageous to supplement certain components with other components for various reasons which will be apparent to those skilled in the art. It may be advantageous to perform steps disclosed herein in a different order, or elect not to practice certain steps under certain circumstances or for particular reasons. For example, pumps of the type described herein can be re-used after activation. In one such approach, a pump can be dried to remove activation liquid absorbed in the polymer layer so that the polymer layer shrinks back to a pre-activation configuration. Additional activation solution can be re-loaded, in some embodiments, to the upper basket, e.g., the upper basket 154 in FIG. 1A, so that the pump can be activated again, or a plurality of times. Mechanical valves can be used to drive activation fluid to the polymer layer as an alternative to the hydrogel valves described herein; thus, pumps according to such an embodiment can be activated manually or by controlling the mechanical valves to activate the pump. In one embodiment of a miniature pump, the dispensable fluid, e.g., dispensable fluid 120 in FIG. 1A is a liquid sealant that can be used to seal a negative wound pressure therapy wound dressing or ostomy wafer. In one embodiment, a pump of the type described herein can be assembled into an operative configuration using ultrasonic welding techniques known in the art.

Miniature pumps such as those described herein can have additional uses beyond what has been described herein. It will be understood that the functionality of the disclosed pumps can be accomplished using the disclosed components; however, those components can be scaled, modified, or adapted to fit other uses. For example, a miniature pump can be used in the practice of balloon angioplasty. In such a use, a pump having features similar to those described herein can be routed through a catheter to a treatment site, e.g., an arterial or venous blockage or damage site. In this embodiment, the pump can be configured to pump air or another gas to an angioplasty balloon, which may be connected directly to an exit port of the pump or remotely positioned on a guide catheter or other instrument. The pump can be triggered by an environmental stimulus, such as a magnetic field, electrical current or other stimulus, to cause the pump to activate and thereby inflate the balloon so that a medical procedure such as arterial repair can be performed. Micromachining techniques can be used in this and other embodiments to manufacture pump components on a scale suitable for angioplasty or other medical procedures, or according to a particular intended use.

Various embodiments may include structures or compositions, or combinations thereof for activating a miniature pump. For example, referring to FIGS. 1A and 1B, the upper pump body 150 includes upper basket 154 and lower basket 158; the upper basket 158 includes an activation solution 166 which can be released upon the expandable polymer layer 140 when the plug layer 145 responds to an environmental stimuli. For example, the plug layer 145 can shrink in size in response to externally-applied heat. The expandable polymer layer 140 can expand in size when it is exposed to the activation solution 166. As described herein, the expansion of the polymer layer 140 can urge the diaphragm 131 into the confines of the lower pump body chamber 107 and thereby force the dispensable fluid 120 out of the pump 100 via the hollow passage 115 and outlet port 116. Other structures or compositions, or combinations thereof are described herein and will be apparent to those skilled in the art.

Thermoresponsive Skin Barrier Appliances

Ostomy leakage can occur for a variety of biological reasons, such as tissue breakdown around the stoma; infection; patient weight loss or gain; construction of the stoma including adequate height of the stoma; contours (e.g., crevices, folds, wrinkles) of the abdomen; moisture around the stoma, if the skin is denuded or if the skin is not dried adequately prior to an ostomy pouch being applied; condition of the peristomal skin; failure of adhesive between product and skin; allergic reaction to adhesives; the patient's lifestyle and activity level; perspiration and need to change ostomy products frequently; incorrect sizing of the appliance to the stoma; inability of certain patients to care for themselves; the characteristics (e.g., chemistry) of effluent, which can depend on the type of stoma, e.g., colostomy, ileostomy, urostomy, etc.; mis-aligned or off-center placement of stoma, relative to the appliance port; the patient's psychosocial adjustment to having a stoma; and other reasons. Furthermore, ostomy leakage can occur from non-biological events, such as breakdown of the ostomy wafer, inefficient sealant, sealant breakdown, and other reasons. So-called 'silent leakage' can occur when the skin barrier of the ostomy erodes and the skin is exposed to effluent, even though there may be no visible signs of leakage. So-called 'Frank leakage' can occur when effluent leaks through the skin barrier, such as when the skin barrier is improperly fit with the stoma, a fold or skin contour exists between the barrier and abdominal wall, or disbanding between the skin and the adhesive barrier occurs.

Figure 10A:
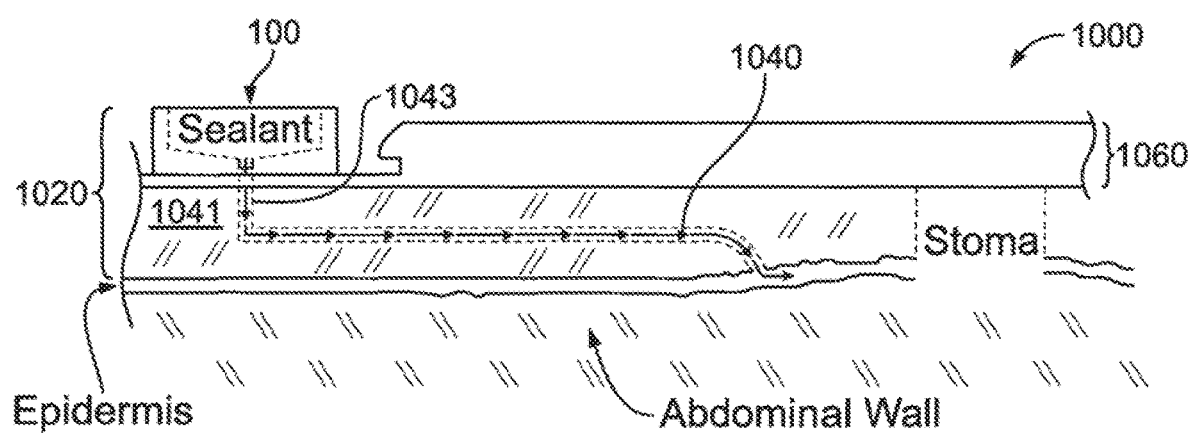
FIG. 10A illustrates a thermoresponsive skin barrier appliance according to one embodiment.

Referring now to FIG. 10A, a portion of a thermoresponsive skin barrier appliance 1000 (hereinafter "appliance" is shown in a side-view according to one embodiment. FIG. 10A illustrates a general operating principle of the appliance 1000, according to one embodiment, while the following figures and description provide further details of its configuration and use.

In general, an appliance 1000 can provide a stoma patient control in the ability to manage a stoma opening related to a colostomy, urostomy, ileostomy, or other procedure. Potentially embarrassing leakage events can be minimized if a patient is given an alert that leakage is impending; the patient can then change the ostomy barrier, if necessary, which can increase peace-of-mind and lead to greater quality of life.

Other advantages can include: a reduction in peristomal skin complications by reducing skin exposure to urine, mucus, and/or feces; an improvement in adjusting to physiological and psychological changes associated with a recent ostomy procedure (e.g., body mass increase or decrease, stoma retraction, hernia, prolapse, and other complications); and providing a toolkit of solutions for nurses, doctors, and other health care providers, where the toolkit can provide solutions for caring for different types of patient physiologies, e.g., skin contours, size, propensity for sweating, etc., or for those caretakers who may have limited access to their patients, e.g., due to a distance to a care facility or work schedule conflicts.

The illustration of FIG. 10A shows a portion of the appliance 1000 bonded to the epidermal skin layer of a patient, over the abdominal wall, as noted. The appliance 1000 includes a hydrocolloid layer 1041 having an adhesive applied to the bottom side to allow the appliance to be adhered to the patient's skin, as shown. In this embodiment, the appliance 1000 includes a substrate platform 1060 that includes at least one moisture sensor, in this example configured as a leakage sensor (not illustrated in FIG. 10A) configured to detect leakage from generally around the stoma area, and at least one micropump, e.g., micropump 100, configured to be responsive, e.g., thermoresponsive, to the leakage detection system as described herein. In this embodiment, the micropump 100 is in signal communication with the leakage detection system and can be activated by the leakage detection system to cause sealant to be expelled from the micropump 100 into a main sealant conduit 1043. The main sealant conduit 1043 is in fluid communication with one or more microchannels 1040 which are configured to transport dispensable fluid 220, in this example, sealant, to the stoma area, as shown.

Figure 10B:
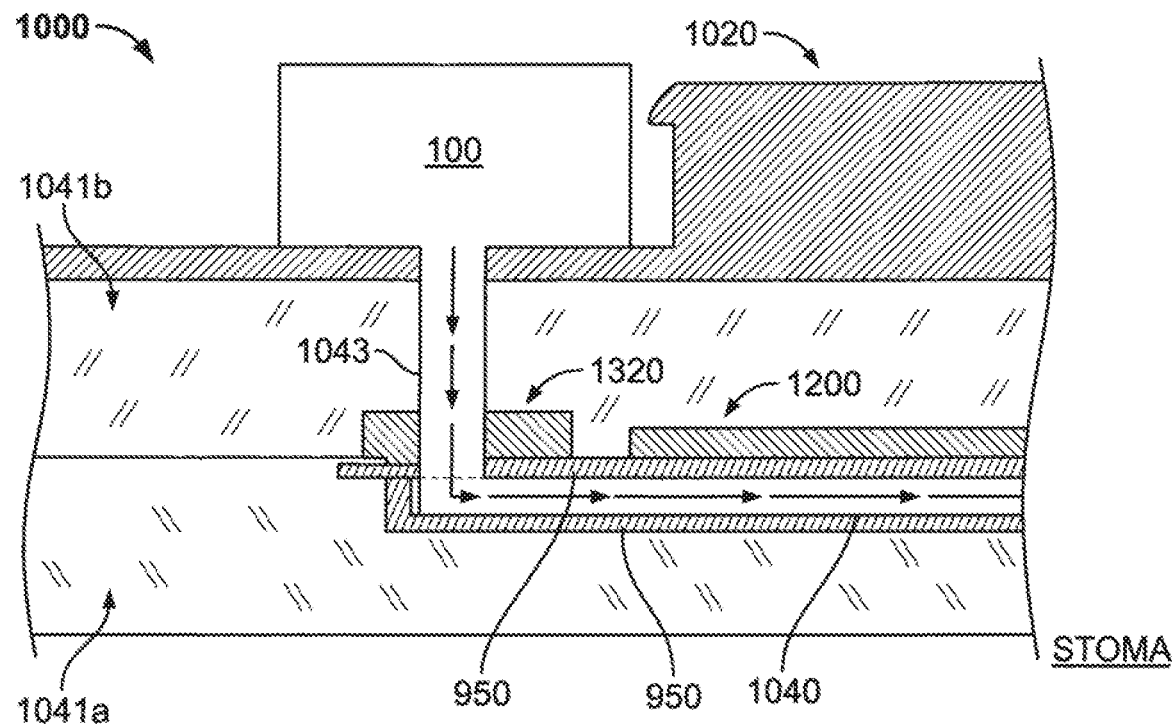
FIG. 10B shows a side elevation view of a thermoresponsive skin barrier appliance according to an alternative embodiment.
Figure 10C:
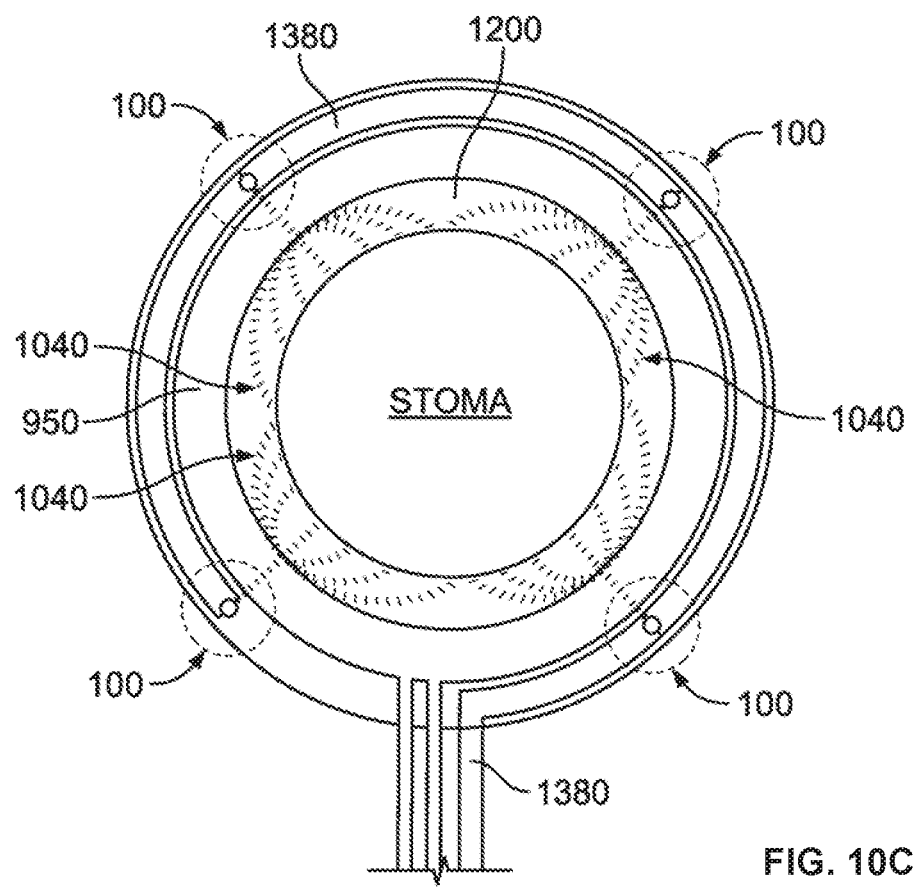
FIG. 10C illustrates a top view of the thermoresponsive skin barrier shown in FIG. 10B.

FIGS. 10B and 10C shows a side-elevation and a top view, respectively, of a portion of the appliance 1000 according to one alternative embodiment. In this embodiment, a sensor/microchannel insert 950 is juxtaposed between first (1041a) and second (1041b) hydrocolloid layers to provide the capability of sensing stoma leakage and dispensing sealant to the stoma area. In this embodiment, the sensor/microchannel insert 950 is a two-layer device including a polyimide, polyether ether ketone (PEEK) or a transparent conductive polyester film substrate. A moisture sensor configured as a leakage sensor circuit 1200 is printed on a top portion of the sensor/microchannel insert; an oppositely disposed, bottom portion of the sensor/microchannel insert includes one or more microchannels 1040 in fluid communication with micropump 100 and configured to deliver dispensable fluid 220, in this example, a sealant from the micropump 100 to the area generally at or about the stoma. The micropump 100 is disposed on flange member 1020 and activated by a heating assembly 1320 as described in greater detail herein. The heating assembly is heated by heating assembly circuitry 1380 as described in greater detail herein.

The leakage sensor can be printed using conductive polymer ink, although other methods can be used to achieve the same or similar results and functionality. The microchannels can be implemented by machining a notch in the insert substrate and applying a cover layer over the substrate or fabricating a 3D structure on the insert substrate.

For example, 3D printing methods can be used to incorporate the microchannel into the insert. In this and other embodiments, the cross-section of the microchannel can be configured as a rectangular shape, circular shape or an optimal geometry that minimizes sealant flow resistance. The insert can connect the micropump output port 216 to the microchannel.

In one embodiment, the sensor/microchannel insert can be fabricated by inserting the micropump 100 through the wafer flange 1020 into the hydrocolloid layer 1041*b* and into the insert assembly. A pump entry hole can be fabricated in the insert to facilitate the output port of the micropump 100. In one embodiment, the micropump can include an exit nozzle which provides fluid communication between the output port of the micropump and the entry hole. Referring to FIG. 10C in particular, in this embodiment, the leakage sensor is printed on the top side of the insert and includes a plurality of micropumps 100 (in this example, four per insert to provide stoma sealant coverage) each with a dedicated microchannel network 1040. The microchannels can be fabricated on the bottom of the insert. The insert also incorporates pump heater circuitry to trigger pump dispensing. The pump heater circuit can be printed using conductive polymer ink, among other approaches.

Delivery of sealant to the stoma area can stop the pending leak and reduce the likelihood of further leaks from occurring by filling the space between the hydrocolloid layer 1041 and abdominal wall, forming a substantially impervious barrier to fluid flow, and maintaining the integrity of the seal. An appliance of the type described herein can be configured to deliver sealant in the area between any skin folds, scar lines or uneven skin surfaces where leakage around the appliance could occur.

Figure 11:
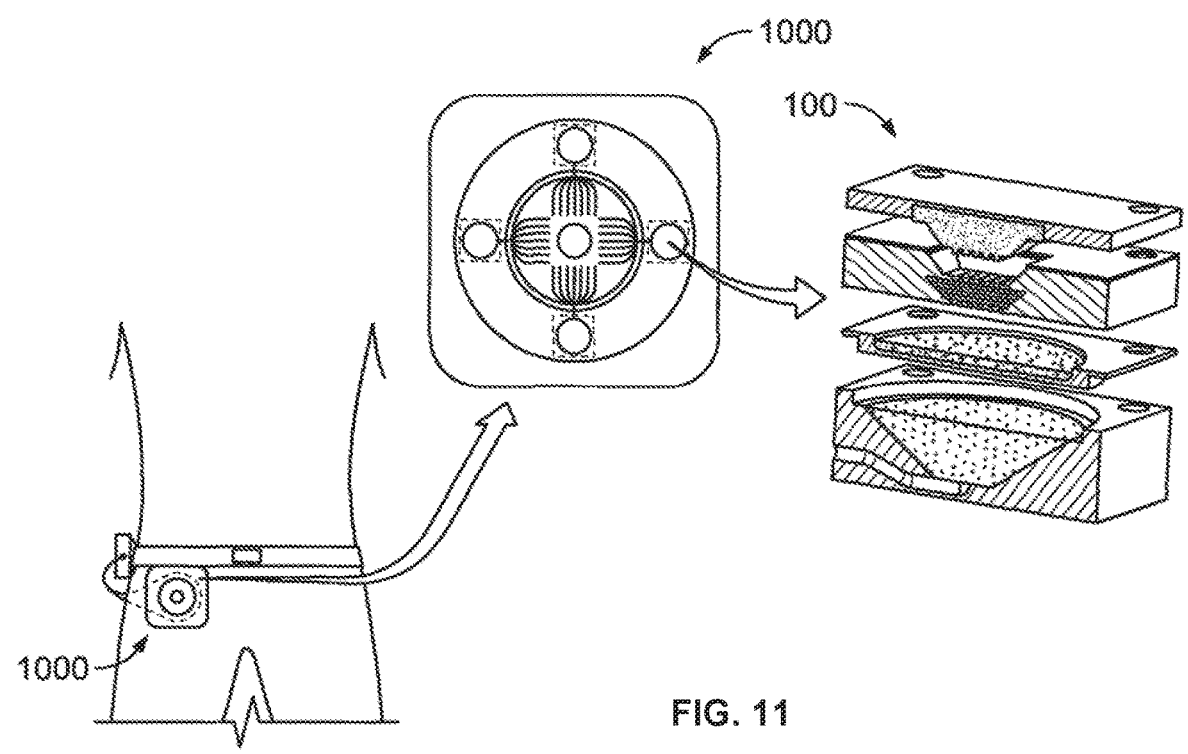
FIG. 11 illustrates a thermoresponsive skin barrier appliance according to one embodiment.

Referring now to FIG. 11, the thermoresponsive skin barrier appliance 1000 is shown in greater detail, according to one embodiment. In this embodiment, the appliance 1000 includes a wearable assembly including a wafer for covering and sealing an ostomy, one or more reservoirs of sealant in fluid communication with the wafer, one or more systems of pumps and fluid conduits for transporting the sealant from the one or more reservoirs to the ostomy site, and one or more leakage sensors disposed on or about the wafer configured to detect ostomy leakage and activate the one or more pumps to seal the ostomy against a portion of the wafer. In one embodiment, the appliance 1000 can include one or more ostomy leakage detection systems capable of alerting the ostomate of a "pending" leak. The alert can motivate the wearer to change the ostomy wafer, which can reduce effluent exposure, thus reducing the risk of skin breakdown. In this embodiment, the appliance 1000 is shown adhered to the torso of a patient over an ostomy site and utilizes at least one miniature pump, e.g., pump 100 as described herein. It should be understood in the following disclosure that other, alternative pumps can be used and the appliance 1000 is not necessarily limited to use of the pumps as described herein.

Figure 12:
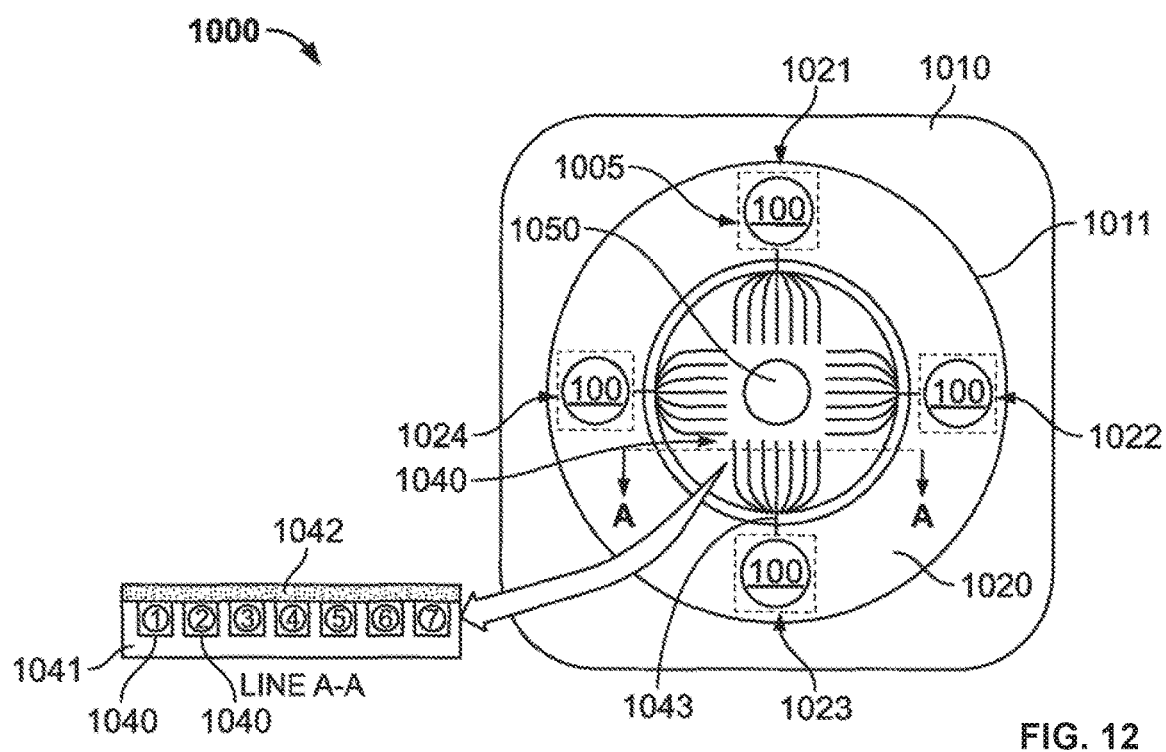
FIG. 12 illustrates a thermoresponsive skin barrier appliance according to one embodiment.

Referring now to FIG. 12, a top-down plan view of the appliance 1000 is illustrated according to one non-limiting embodiment. In this embodiment, the appliance 1000 is configured to cover an ostomy site to reduce the likelihood of leakage, and, if leakage should occur, respond by deploying a bio-compatible sealant into or about the stoma area.

In this embodiment, the appliance 1000 includes a wafer 1010, e.g., an ostomy wafer configured to be applied to a patient about an ostomy site. For example, the wafer 1010 can include adhesives on a bottom side, e.g., the opposite side from the top side as illustrated, so that the appliance can be adhered to the patient for a period of time. The adhesive material can be, e.g., one that reduces the likelihood of skin irritation resulting from prolonged contact, such as those adhesives used on bandages and the like. One preferred adhesive is sold under the "Uro-Bond IV Silicon-Based Adhesive" product name (product No. 500403) by Urocare Products, Inc., Pomona, Ca.

In this embodiment, the appliance 1000 includes a flange member 1020 engaged with a centrally-located aperture within the wafer 1010. In this embodiment, when assembled in an operational configuration, the flange member 1020 includes four sealant delivery assemblies 1005, wherein each assembly 1005 includes a micropump, e.g., micropump 100 as previously described; a main sealant conduit 1043 in fluid communication with an exit port of the micropump, e.g., outlet port 116 as previously described; and a microchannel array 1040 in fluid communication with the main sealant conduit 1043.

In this embodiment, each of the individual microchannels, e.g., microchannel 1, 2, 3, etc. as illustrated in the enlarged cross-sectional view of the microchannel array 1040 is configured to discharge sealant at or in the vicinity of the ostomy site when the one or more pumps 100 are activated as described in greater detail herein. In one embodiment, the main sealant conduit and the microchannels 1040 can be pre-loaded with sealant, where activation of the pump 100 can cause the pre-loaded sealant to be expelled at or near the vicinity of the ostomy. It should be understood that while a plurality of microchannels disposed as illustrated in FIG. 12 can provide advantageous dispersion of sealant at or near the ostomy site, such a configuration is one of many possible options for achieving the same objective. For example, in an alternative embodiment, one or more of the main sealant conduits 1043 can be in fluid communication with one or more ring-shaped, perforated microchannels configured to surround the ostomy site (not illustrated in FIG. 12). In such an embodiment, activation of one or more micropumps 100 can cause sealant to be expelled around the ostomy site to prevent leakage.

In this embodiment, the main sealant conduit 1043 and the microchannel array 1040 are disposed in a hydrocolloid layer 1041. The dimensions of the conduits and the microchannels can be chosen according to preference or to achieve desired performance characteristics such as a desired sealant flow rate. In some cases, the dimensions can be chosen according to the kind, type, or a physical property of the sealant being delivered. In one embodiment, the microchannels have cross-sectional dimensions of about 2 mm by about 2 mm.

In this embodiment, the main sealant conduit 1043 and the microchannels can be engraved into the hydrocolloid layer, e.g., through a machining process, although other approaches can be used. In this embodiment, a laminate layer 1042 overlaps the hydrocolloid layer 1041 to provide the "top" of the microchannels and sealant conduits, wherein the laminate layer 1042 has a thickness of about 0.5 mm. The thickness of the laminate layer 1042 can be chosen according to preference or to achieve desired performance characteristics.

Figure 13A:
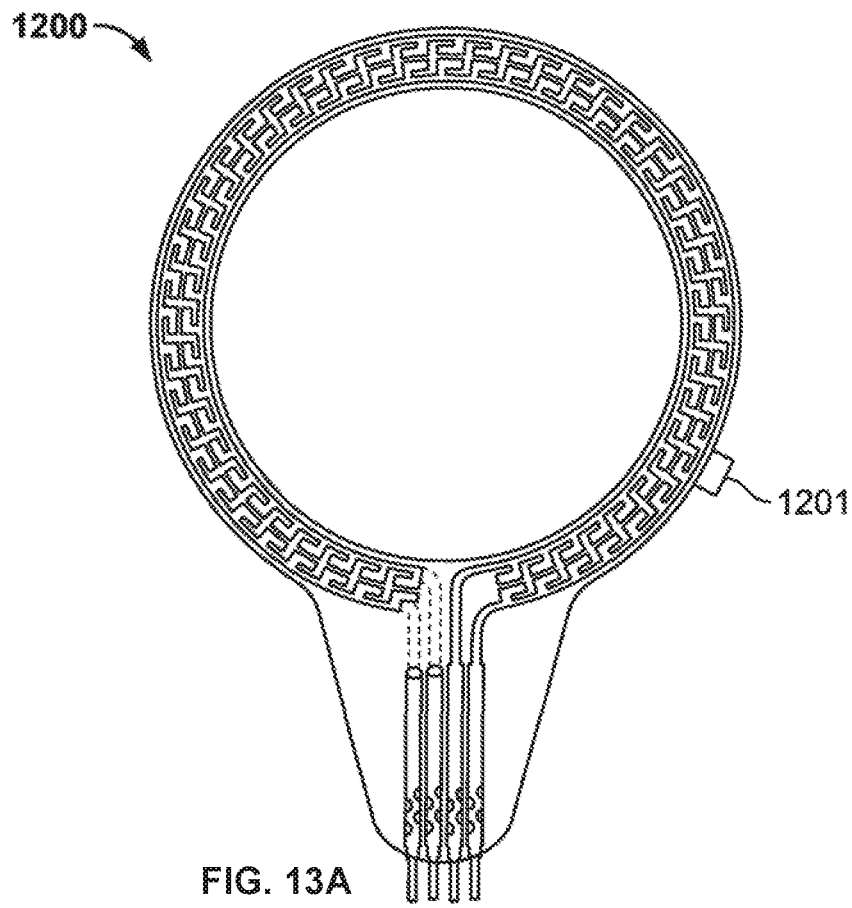
FIG. 13A illustrates a leakage sensor of the appliance according to one embodiment.
Figure 14:
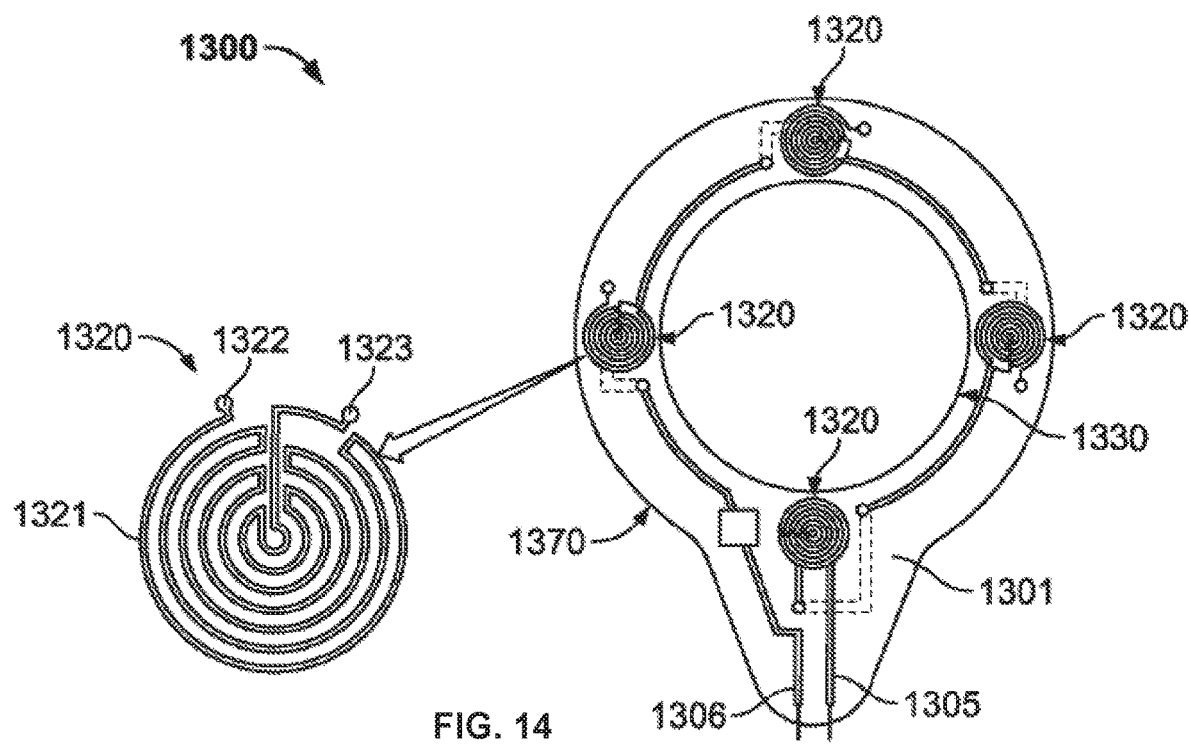
FIG. 14 illustrates a heating element array assembly of the appliance according to one embodiment.

Referring now to FIGS. 13A and 14, an exploded view of the flange member 1020 is illustrated according to at least two embodiments. In the description that follows, in general, the flange member 1020 includes components for detecting and addressing ostomy leakage, including one or more micropumps, one or more heating assemblies for activating the one or more micropumps, and one or more temperature sensors. FIGS. 13A and 14 illustrate alternative embodiments of a flange member 1020 where the various flange components can be provided in a one- or two-layer approach as described in greater detail below. In both the one- and two-layer flange assemblies, FIG. 13A and FIG. 14 respectively, each of the components is configured using circuitry to be in electronic communication with each other, in communication with an electronic control module that controls various aspects and functions of the assembly 1000, or a combination thereof. Some of the components of the flange member 1020 are now described so that they may be understood when describing their integration into various flange member embodiments.

Figure 13B:
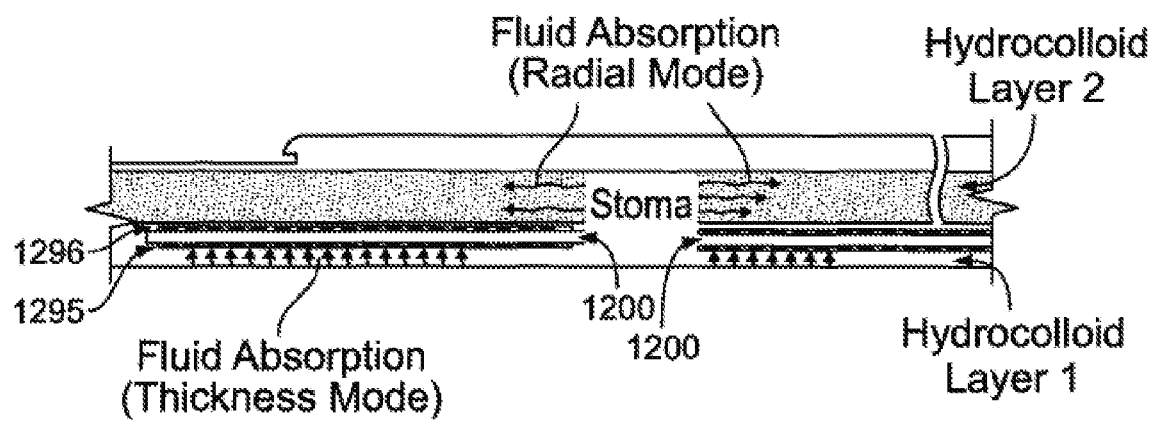
FIG. 13B illustrates a top-view of a sensor array according to one embodiment.
Figure 13C:
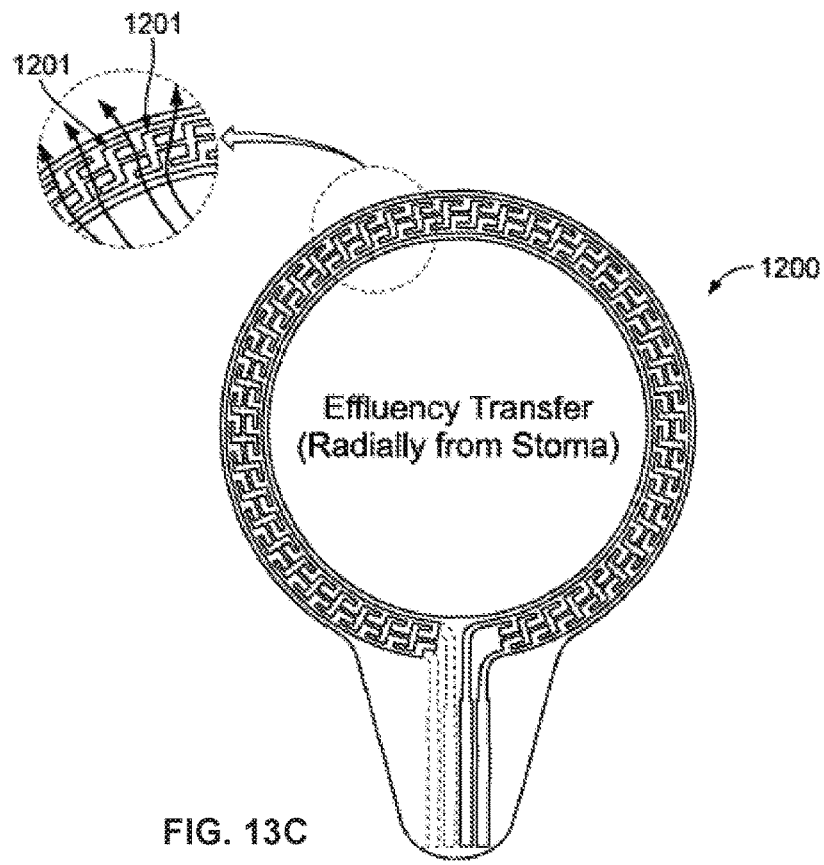
FIG. 13C illustrates a heating element array assembly of the appliance according to one embodiment.

Referring now to FIGS. 13A, 13B, and 13C, a leakage sensor 1200 is shown according to one embodiment. Leakage sensor 1200 can detect a flow of moisture and correspondingly trigger a pump, e.g., pump 100 or 200 to dispense a flowable substance such as a sealant. Referring first to FIG. 13A, in this embodiment, the leakage sensor 1200 includes two electrochemical arrays 1201 disposed on top and bottom surfaces of a non-conductive polymeric substrate, respectively, wherein each array includes a plurality of adjacently-disposed, leakage-sensing electrode pairs. Referring specifically to FIG. 13C, in this embodiment, a first electrode connector strip 1205 is circumferentially disposed generally about the perimeter of the substrate. The connector strip 1205 is in electrical communication with a plurality of "L" shaped individual electrodes 1206 extending therefrom as illustrated. A second electrode connector strip 1207 is concentrically aligned with the first electrode connector strip 1205 and similarly includes a plurality of "L" shaped individual electrodes 1208 adjacently disposed to the individual electrodes 1206 of the first connector strip 1205 as illustrated. In this embodiment, the sensor electrodes 1206, 1208 of each respective connector strip can be interdigitated with one another, and are preferably arranged in a curved linear array as illustrated. In this embodiment, each array includes 46 electrode pairs which provides sufficient leakage detection; however, it should be understood that a sensor array can include a greater or lesser number of electrode pairs to provide desired functionality.

Referring back to FIG. 13B, in this embodiment, leakage detection is accomplished by the interdigitated electrodes of the sensor array 1200 in cooperation with the absorptive properties of one or more hydrocolloid layers adjacent thereto. In this embodiment, the measurable electrical impedance of the hydrocolloid is a function of the amount of absorbed exudates; accordingly, leakage resulting from, e.g., wafer breakdown can be detected by measuring a difference in electrical impedance between one or more electrodes. For example, a reduction (increase) in impedance increases (decreases) the conductivity between electrode pairs; thus a relative amount of hydrocolloid absorption can be quantified for a given region of the sensor array 1200 by analyzing adjacent electrode pairs, which can be interpreted to indicate a stoma leakage event.

In this embodiment, each electrode pair has dimensions of about 1/8"×about 1/16" (length×width) spaced approximately 1/32" apart and, when used in cooperation with other electrical components described in further detail below, is capable of causing an electronic signal to be generated when moisture absorbed by the hydrocolloid contacts at least one of the arrays 1201. It should be understood that the dimensions of the electrochemical sensors can be adjusted or selected as necessary to meet desired device characteristics such as leak detection performance, fit, style, or other considerations. In this embodiment, the circuitry of the leakage sensor 1200 is printed on a five mm-thick polyester film substrate 1210; the components of the circuit can be printed using conductive polymer ink, although other methods can be used to achieve the same or similar results and functionality. Likewise, a leakage sensor 1200 can include a greater or less number of electrochemical sensors as necessary for a particular application; or the electrochemical sensors may be exchanged for a sensor of a different type.

The multi-electrode design of the sensor 1200 can provide advantages over sensors using only a single pair of electrodes. For example, each electrode pair acts as an independent sensor element that is capable of providing an averaged sensor output signal over a given region of the sensor 1200. Signal averaging can reduce operational electromagnetic interference (EMI) noise, which can lead to improved signal-to-noise ratios during operation. In another example, The multi-electrode design can also provide signal redundancy to increase system reliability; for example, if one pair of electrodes fails or is partially inactivated, signal-averaging and the presence of multiple other electrode pairs reduces the likelihood of complete system failure to detect leakage events.

Figure 16:
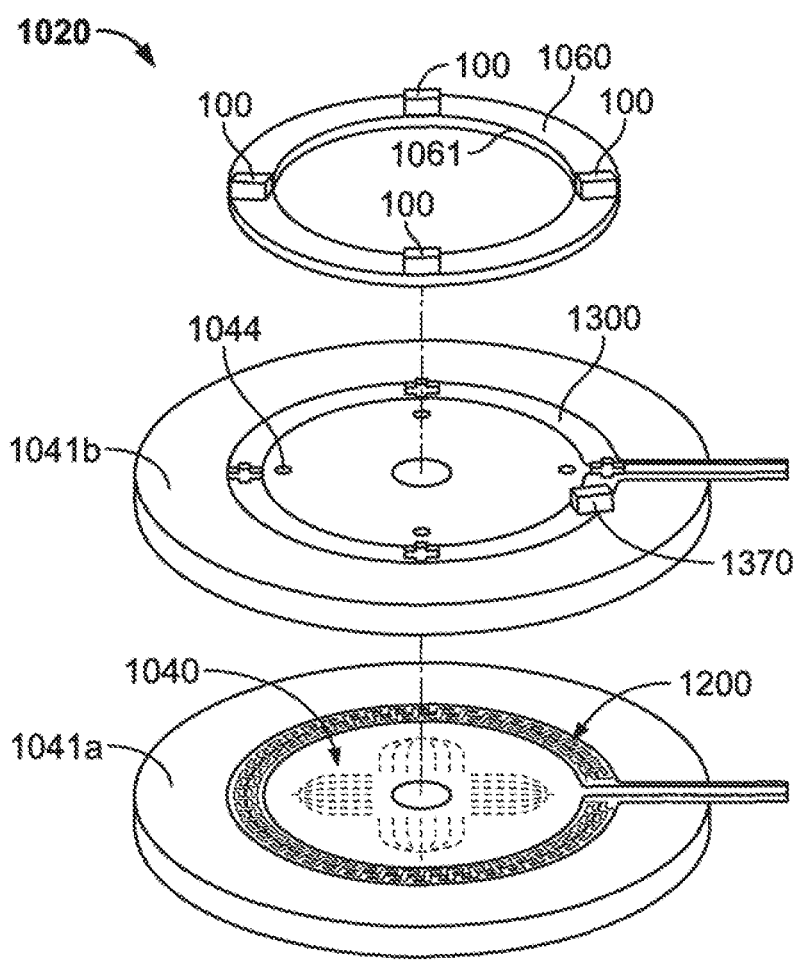
FIG 16. illustrates a flange member of the appliance according to an alternative embodiment.

Referring to FIGS. 13B-13C, in this and other embodiments, in particular the embodiment of FIG. 16 shown and described herein where the flange member 1020 includes dual hydrocolloid layers, the leakage sensor 1200 is capable of detecting leakage traveling through the hydrocolloid layers in different directions. It should be understood, however, that such functionality is not necessarily required. In such an embodiment, the leakage sensor can detect effluent propagating in a "radial mode"—e.g., through a hydrocolloid layer in a radial direction from the stoma outward; or in a "thickness mode"—e.g., effluent traveling vertically from the first (bottom) hydrocolloid layer to the second (top) hydrocolloid layer as illustrated in FIG. 13B.

In this embodiment, the leakage sensor 1200 can be configured to detect vertical effluent propagation (thickness mode) in the first (bottom) hydrocolloid layer; and radial effluent propagation (radial mode) in the second (top) hydrocolloid layer. This can be accomplished in several ways; for example, one electrochemical array can be placed on a bottom side of the substrate 1210 to detect vertical effluent propagation (denoted 1295 in FIG. 13B), and another, identical electrochemical array can be placed on an opposite, top side of the substrate 1210 to detect radial effluent propagation (denoted 1296 in FIG. 13B).

FIG. 12 B shows a magnified portion of leakage sensor 1200, where stoma effluent is illustrated as propagating radially from the stoma outward, across electrochemical array located on the topside of the sensor 1201. In this and other embodiments, the individual sensors of the array on top and bottom sides of the sensor 1200 can be adjacently placed and orthogonally oriented to maximize effluent detection for peak leakage protection.

In this embodiment, a leakage sensor capable of operating in "radial" or "thickness" mode, as described, can provide valuable information to a caretaker or the ostomy patient regarding the type of leak that is occurring or that may be imminent. For example, leakage detection circuitry (described in greater detail herein) can be configured to provide a signal correlating to a detection signal in the first (bottom) or second (top) hydrocolloid layer. Such information may be valuable to the patient or wound ostomy continence nurse (WOCN) in discriminating against false signals that may be caused, e.g., by excessive sweating from the skin, wafer fitting issues (i.e. due to folds, creases in abdominal skin wall or new stoma construction problems. In this case, if signals were only detected by the bottom electrochemical array and not the top, the patient may conclude they need to check the fit and bonding of the ostomy wafer.

Referring now to FIG. 14, a heating element 1320 is shown according to one embodiment. FIG. 14 also illustrates placement of a plurality (in this example, four) heating elements circumferentially disposed and serially-connected about a substantially circular, flexible substrate 1301 to form a heating element array assembly 1300. In this embodiment, the heating element 1320 is formed of a conductive electrode 1321 having input (1322) and output (1323) terminals and is configured to deliver at least enough thermal energy to cause activation of a pump as described herein, e.g., micropump 100. In this embodiment, the heating element 1320 is configured in a substantially circular shape; however, other alternative shapes such as disc or ellipse shapes can be substituted as desired.

The conductive electrode 1321 can be formed of any desired material; however, the choice of that material can depend on providing suitable electrical conductivity and mechanical strength. Preferred electrode materials include, but are not limited to: platinum, etched foil, micro-thin wire and polymer-thick-film (PTF). Platinum can be a most-preferred material as it offers good electrical conductivity and is substantially inert to degradation resulting from contact with body fluids. Utilizing a PTF may offer a low manufacturing cost.

The flexible substrate 1301 of the heating array assembly 1300 can be formed of any desired material, and the conductive electrode can be placed thereon or integrated therein. Preferred substrate materials are those that are lightweight and provide low thermal mass, a high bending radius, a high dielectric strength, and low current leakage. For example, and without limitation, suitable flexible substrate materials can include polyester, silicone rubber, polyimide, polyimide films, e.g., those sold under the Kapton brand by DuPont, Inc., and PTFE.

In general, the heating element array assembly 1300 can have the following advantageous attributes, however, none of the attributes are necessarily critical: 1) a high wattage density (e.g., up to 50 watts per square inch); 2) a low thermal mass (for efficient heat transfer); 3) fast ramp-up times; 4) an very thin (e.g., 4 mm thick) substrate to provide flexibility in conforming to patient's physiology; 5) lightweight construction, to add little weight to the assembly 1000; the ability to incorporate temperature sensors and heating elements into a common substrate; and 7) low-cost fabrication. PTF heating element array assemblies can be quickly prototyped and implemented in high volume using screen-print or ink jet printing techniques. In one embodiment, the heating element 1320 can be designed to activate the pump 100 (e.g., trigger adhesive release) by raising the pump temperature through conductive, radiant, or direct heat transfer.

In this embodiment, the heating array assembly 1300 includes at least one temperature sensor 1370. The temperature sensor 1370 can be configured to monitor the sensor of one or more of the heating elements 1320 to provide a patient safety factor. For example, the at least one temperature sensor 1370 can be configured in cooperation with an electronic circuit to prevent a heating element from overheating, e.g., by shutting it off if a pre-selected threshold temperature is sensed. In a preferred embodiment, a temperature sensor 1370 is one offering a low profile, fast response, high sensitivity, and low cost.

One non-limiting, preferred embodiment of a heating element array assembly 1300 includes four serially electronically-connected, circumferentially-disposed PTF-printed heating elements 1320 printed on a five mm thick polyester film substrate using a conductive printing material, wherein the film substrate includes a central aperture 1330, and an temperature sensor 1370 configured to be capable of controlling power to the heating elements upon sensing a pre-selected threshold temperature, e.g. as illustrated in FIG. 14. In this embodiment, the heating array assembly 1300 includes circuit leads 1306, 1306 for operatively connecting with other components of the appliance 1000. In this and other embodiments, other heating elements can be substituted for those previously described. For example, heating elements can utilize surface-mounted, thick-film resistor elements as is generally known in the art. A surface mount design approach may offer higher electrical resistance per unit area than PTF circuits, which may provide a patient safety aspect.

Figure 15:
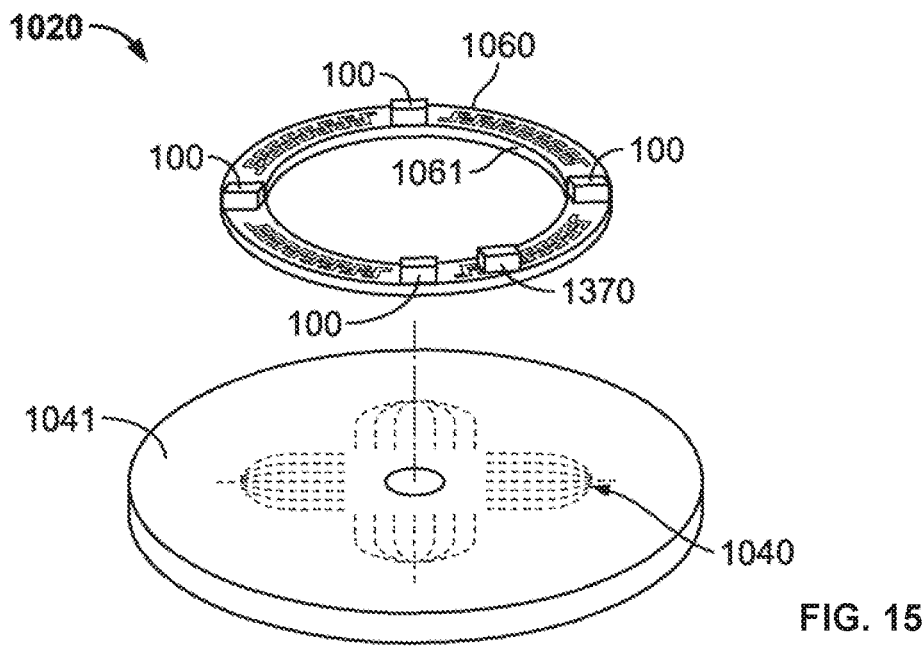
FIG. 15 illustrates a flange member of the appliance according to one embodiment.

Referring now to FIG. 15, an exploded-view of a flange member 1020 is illustrated according to one embodiment. In this first of two disclosed flange member embodiments, the flange member 1020 includes a hydrocolloid layer 1041 configured with the aforementioned main sealant conduit 1043 and microchannel array 1040 of each sealant delivery assembly 1005 as previously described. The flange member 1020 further includes a ring-shaped substrate platform 1060 having disposed thereon previously-described components for detecting ostomy leakage and activating the one or more micropumps 100 in response thereto.

In this and other embodiments, the hydrocolloid layer 1041 can be protected from damage during handling/installation or exposure to the environment by a surrounding clear polyimide or polyurethane layer. Such a layer can also provide a selected amount of stiffness in the hydrocolloid layer. In one embodiment, the hydrocolloid layer includes a polyimide or polyurethane layer from about 3 mm to about 5 mm in thickness.

For example, in this embodiment, the substrate platform 1060 includes four circumferentially-disposed micropumps 100 as illustrated, each micropump 100 being disposed in proximity to a heating element 1320 (not visible in FIG. 13A) and configured such that the expellable contents of each micropump 100 is in fluid communication with its respective main sealant conduit 1043. In this and other embodiments, the placement of each micropump 100 is such that it can be activated, e.g., caused to expel its contents such as sealant into its associated sealant delivery assembly 1005, by the activation and warming of the proximal heating element 1320. In one example, each micropump 100 can be disposed over its corresponding heating element 1320.

In this embodiment, the substrate platform 1060 further includes at least one temperature sensor 1370 to provide an aspect of patient safety as previously described. The substrate platform 1060 can be a semi-rigid framework, e.g., formed of a suitable plastic, metal, or other material, and, in this embodiment, is ultrasonically welded to the hydrocolloid layer. In this embodiment, the inner wall 1061 of the substrate platform 1060 is configured to receive a locking member of an ostomy pouch (not illustrated in FIG. 15 or 16). In a preferred embodiment, the inner wall 1061 is configured to receive an ostomy pouch using a press-on or snap-on locking configuration to provide an air-tight seal and eliminate leakage. In a preferred embodiment, the ring member 1060 is a flexible plastic substrate, for example formed of polyimide, polyether ether ketone (PEEK) or a transparent conductive polyester film, although other materials that provide the same or similar functionality can be used as alternatives.

In this and other embodiments, conductive elements of a heating element array assembly 1300 can be printed on the substrate platform 1060 by methods described herein, or by alternative methods. In such an embodiment, such circuitry can be printed on, e.g., a single surface or printed on, e.g., overlapping substrate layers. In the later case, the various components can be in electronic circuit communication with each other as necessary by connecting circuitry through the various substrate layers by known methods.

Referring now to FIG. 16, an exploded-view of a flange member 1020 is illustrated according to an alternative embodiment to that described with respect to FIG. 15. In this embodiment, the flange member 1020 includes a first hydrocolloid layer 1041 having a leakage sensor 1200 disposed thereon. The first hydrocolloid layer 1041 is configured with a main sealant conduit 1043 and microchannel array 1040 as previously described portions of a sealant delivery assembly 1005. A second hydrocolloid layer 1041b includes a heating element array assembly 1300 disposed thereon and is configured to substantially overlap the leakage sensor 1200 and the first hydrocolloid layer 1041a.

In this embodiment, the substrate platform 1061 1060 includes four micropumps 100 disposed thereon and is configured to lockingly engage the heating element array assembly 1300 in an orientation that places each micropump 100 over a heating element 1320 of the heating element array assembly 1300, respectively. The substrate platform 1060 can be configured to lockingly engage the heating element array assembly 1300 by a variety of methods. For example, the substrate platform 1060 can include male thread members configured to be threaded into a corresponding female-threaded receptacle (not illustrated in FIG. 16). Alternatively, in one embodiment, the substrate platform 1060 can have locking tabs extending therefrom that are configured to lockingly engage complimentary locking receptacles disposed on the heating element array assembly 1300 in the aforedescribed orientation. Other methods can be used to lockingly engage the substrate platform 1060 to the heating element array assembly 1300 as desired.

In this embodiment, the second hydrocolloid layer 1041b further includes an aperture, e.g., aperture 1044 in FIG. 16, for each main sealant conduit 1043 disposed on the first hydrocolloid layer 1041a, so as to provide fluid communication between the various layers of the flange member 1020, e.g., between the output port of the pump 100 and the main sealant conduit 1043.

Manufacture of a flange 1020 as illustrated and described with respect to FIG. 16 can be accomplished according to a variety of methods. For example, one approach includes center-aligning the leakage sensor 1200 with the first hydrocolloid layer 1041a, center-aligning the heating element array assembly 1300 with the second hydrocolloid layer 1041b, bonding the first and second hydrocolloid layers together, electrically connecting leakage sensor 1200 to the heating element array assembly 1300, center-aligning and ultrasonically welding the substrate platform 1060 to the second hydrocolloid layer 1041b, and mounting the micropumps 100 on the substrate platform 1060 such that they substantially overlap the heating elements 1320 of the heating element array assembly 1300. It should be understood that the instant manufacture process is one approach of many, and that steps can be performed in different order than those described here. Furthermore, in some cases it can be advantageous to bond the micropumps 100 to the to the substrate platform 1060 prior to welding the substrate platform 1060 to the second hydrocolloid layer 1041b.

In general, manufacture of a single hydrocolloid-layer flange member, e.g., flange member 1020 illustrated in FIG. 15 can integrate one or more micropumps, a leakage sensor, a heater array assembly, and a temperature sensor together on a single substrate to potentially simplify manufacturing and reduce product cost. The leakage sensor and heater array assemblies can be printed as a PTF circuit on an opposite side of the substrate to that of the micropumps, for example. In one approach, a dual-use circuit can be configured to both receive leakage sensor inputs and correspondingly control heating elements to cause micropumps to activate. As previously described, such activation of a micropump can cause sealant to be dispensed to the ostomy site to seal the leak. In one approach, micropumps can be molded into a polyester/polymer substrate and preloaded with sealant prior to welding the substrate to the hydrocolloid layer.

Figure 17:
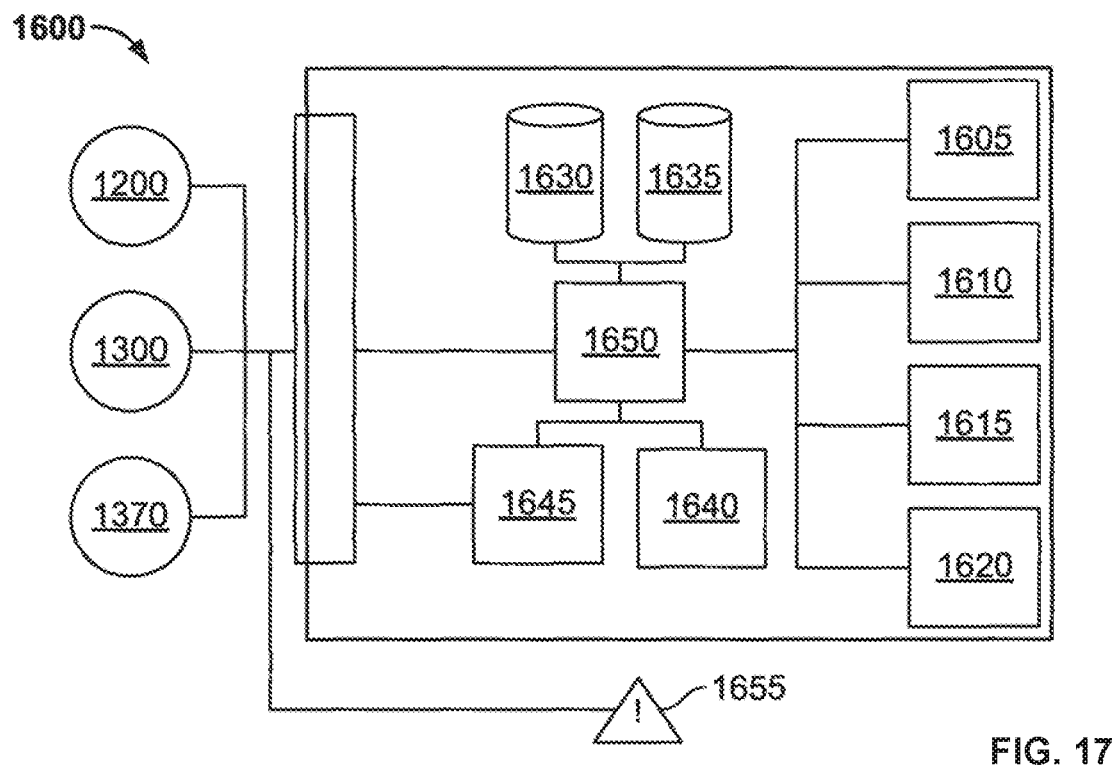
FIG. 17 illustrates a control module of the appliance according to one embodiment.

Referring now to FIG. 17, a microprocessor-based appliance control module 1600 (hereinafter "control module") is illustrated according to one embodiment. It should be understood that the control module 1600 described herein can provide appliance control functions, e.g., sensing ostomy leakage, activating pumps to control leakage, and furthermore collect and analyze data as described in greater detail below using microprocessor-based electronic hardware and circuitry. However, other embodiments may operate autonomously, in that much simpler circuitry can be employed for the basic functions of sensing leakage by the leakage sensor and activating a pump for dispensing sealant to seal the leak.

In this embodiment, the control module 1600 includes five function modules: a data acquisition module 1605, a data analysis module 1610, a bio-alerting module 1615, and a micropump control and power management module 1620. The control module further includes at least one memory module 1625, e.g., RAM, a first data repository 1630 for storing collected data, a second data repository 1635 for storing logic functions, e.g., software, firmware and like instructions for carrying out the various functions of the appliance as described herein, and an input/output (I/O) module 1640 providing signal communication between the control module 1600 and appliance components external of the control module, e.g., leakage sensor 1200, heating element array assembly 1300, temperature sensor 1370, a bio-alert module 1655, an analog-to-digital conversion module 1645, and other components. The control module further includes a microcontroller 1650 for carrying out instructions, analyzing data, sending and receiving control signals, and other functions as will be apparent to those skilled in the art of computer circuitry. It should be understood that each component of the control module 1600 can be in signal communication with each other for the purpose of sharing data, analyzing data, storing data, transmitting signals, etc., as those skilled in circuit design will appreciate.

In this embodiment, the microcontroller 1650 is a low power, 8-bit microcontroller (PIC 18LF) that provides the capability for leakage sensor 1200 data acquisition, processing one or more leakage algorithms, micropump activation via heating element array assembly 1300 and bio-alerting, among other functions. In one approach, the leakage sensor can be configured to produce an analog signal corresponding to an amount of moisture present on or around the leakage sensor 1200; in other words, the signal can correspond to a degree of ostomy leakage ranging from, e.g., no leakage, to full saturation around the leakage sensor 1200. The leakage sensor signal can be measured by the A/D converter 1645 and digitized, e.g., into 12 bits of resolution. In one embodiment, the microcontroller can send an excitation signal to the leakage sensor, collect return sensor array data signals, and process those data to identify leakage events. Subsequently the microcontroller can alert the wearer via auditory or other alerting modalities, and concurrently control one or more heating elements to cause activation of a micropump as described herein to dispense a biosealant to the leakage area.

The microcontroller can perform functions for collecting and analyzing these data, e.g., according to a stored leakage algorithm to determine if a leakage event will occur, or is occurring, and accordingly inform the patient via, e.g., a vibratory cue to take corrective action and replace the assembly 1000 or give authority to activate one or more heating elements on the heating element array assembly 1300 to cause activation of one or more micropumps. In one embodiment, the vibratory cue can be provided by an on-board piezoelectric motor in electronic signal communication with the microcontroller, although other alerting systems can be substituted as desired. In one embodiment, the authority to activate the one or more micropumps can be received by depressing an "automatic dispensing" button on the control module. As discussed herein, activation of a micropump can cause sealant stored therein to be expelled from the pump, travel through the main sealant conduit to the microchannels, and be dispersed about the ostomy leakage area to prevent or reduce further leakage.

In this embodiment, the temperature sensor 1370 can be read by the microcontroller to determine pump activation temperature. A closed loop proportional integral-derivative (PID) algorithm can be used to accurately control pump dispensing. In this embodiment, the control module is in signal communication with at least one component for warning the wearer of an impending leakage or one that is currently underway. For example, when the control module determines such a leak, a signal can be sent to activate a vibratory mechanism placed in contact with the wearer's skin, so that they are notified by vibration of the situation. Alternatively, or in combination, the control module 1600 can include auditory components, e.g., a speaker that similarly emits an auditory warning signal if an ostomy leakage is detected.

Alternatively, or in combination, the module 1600 can include instructions for communicating with other electronic devices. For example, for ostomy patients in a hospital or nursing home setting, the module 1600 can be connected through a USB port to a monitoring station or other device that can alert a WOCN in the event of ostomy leakage. In another example, the control module can include a wireless transmitter/receiver for wirelessly broadcasting leakage data for monitoring or to alert staff that the ostomy patient needs attention. In yet another example, the control module can include logic functions to send usage statistics, appliance status, and other data wirelessly, e.g., using Wi-Fi, Bluetooth, or other communications protocols to a remote device, e.g., a smartphone, tablet, computer terminal, etc. Such information can be sent over any appropriate wired or wireless communication standard, e.g., "Wi-Fi," "Bluetooth," or other protocols. In one embodiment, information can be sent to a user's computing device such as a cell phone or iPad as part of a 'mobile health' (mHealth) interface. In this and other embodiments, the control module 1600 can include other control components, e.g., on/off switches, status indicator lights, low-battery warning indicia, input/output ports, e.g., USB ports for transmitting/receiving data to/from the module 1600, etc., as desired for functionality and user friendliness. The control module 1600 can be powered by any desired modality, e.g., through the use of batteries, capacitors, "plug-in" AC or DC power, etc.

Figure 18:
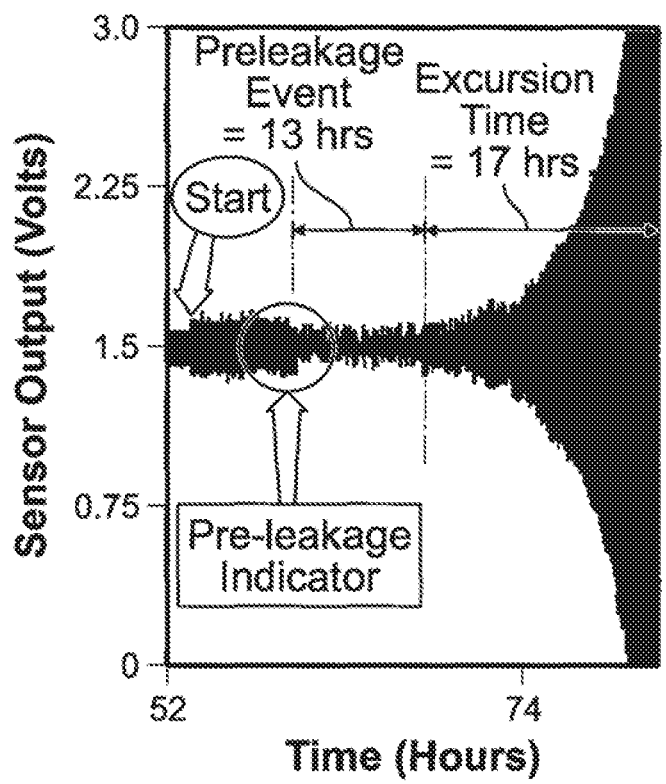
FIGS. 18 and 19 show leakage sensor data according to one data collection method.
Figure 19:
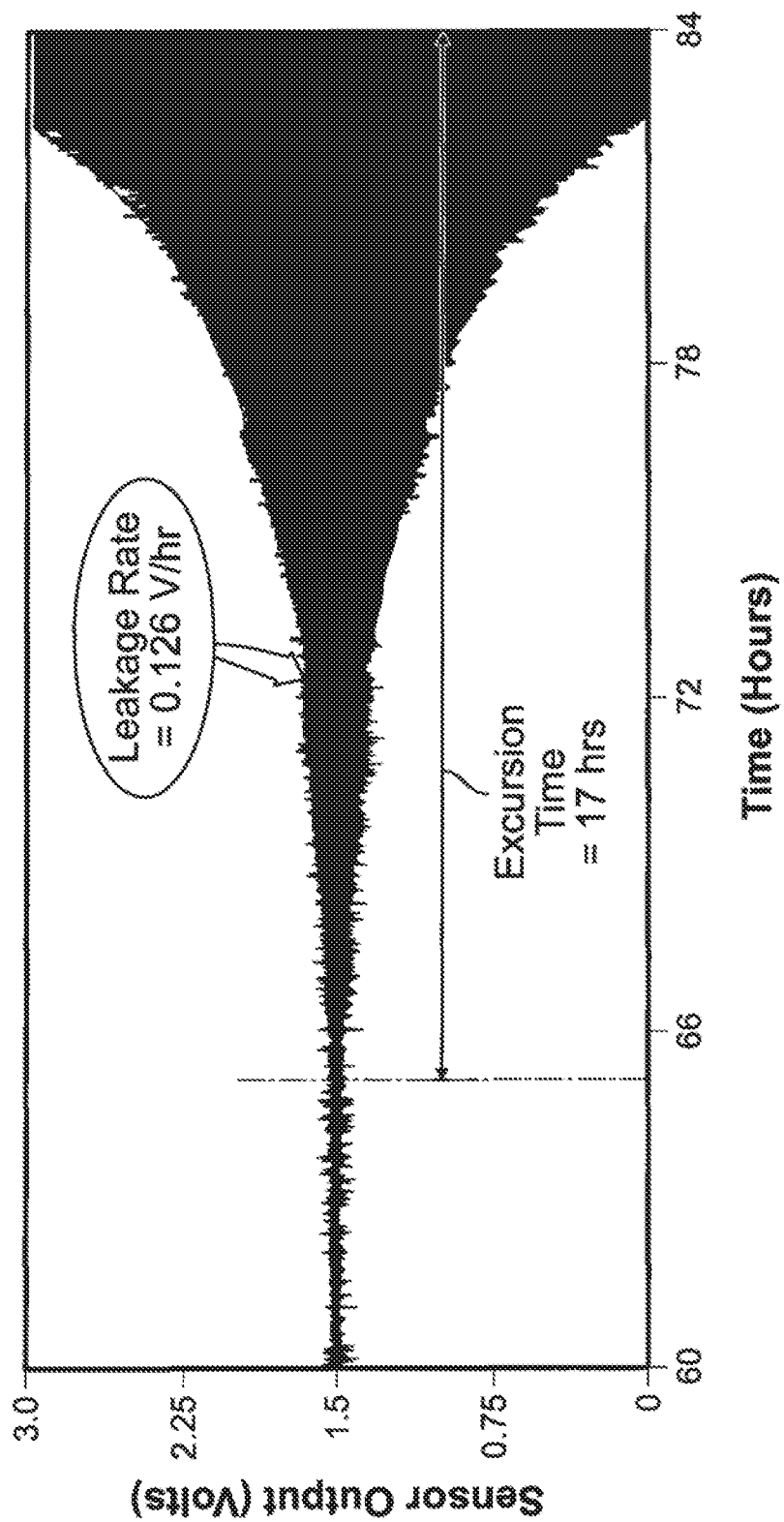

In general, ostomy leakage-related events can be detected by analyzing leakage sensor data for the presence of one or more leakage data patterns. Referring to FIGS. 18 and 19, and without wishing to be bound by theory, it has been discovered that ostomy leakage can be detected by identifying three events: 1) occurrence of a pre-leakage indicator event; 2) a pre-leakage event; and 3) a leakage event giving rise to leakage sensor data having an exponential signal output. It should be understood that this approach is one of many methods for detecting an ostomy leak using an appliance of the type described herein, and therefore should not be considered necessarily required for appliance functionality.

FIGS. 18 and 19 show leakage sensor data collected using a thermoresponsive skin barrier appliance 1000 as described herein on a 46 year-old female colostomy patient. The appliance 1000 was applied to the ostomy site of the patient and monitored for leakage as described herein. In this example, the pre-leakage indicator event shows the transition from when the wafer is unaffected by fluid (new condition) to when fluid absorption starts. It is characterized in part by a level-shift in output voltage approximately in the circled portion of the chart. In this example, the pre-leakage event is approximately 13 hours in duration, and indicated by a voltage level shift which, in this case is caused by a change in the impedance of the electrochemical array and indicates a transition from normal wear to a progressive state of effluence absorption leading to wafer breakdown and loss of adhesion. In this example, the leakage event (excursion) is characterized by exponential signal growth with durations of 90 minutes to days in length. Analysis of the excursion time, which is shown in an expanded view in FIG. 19, reveals a leakage growth rate of 0.126 volts/hour.

Figure 20:
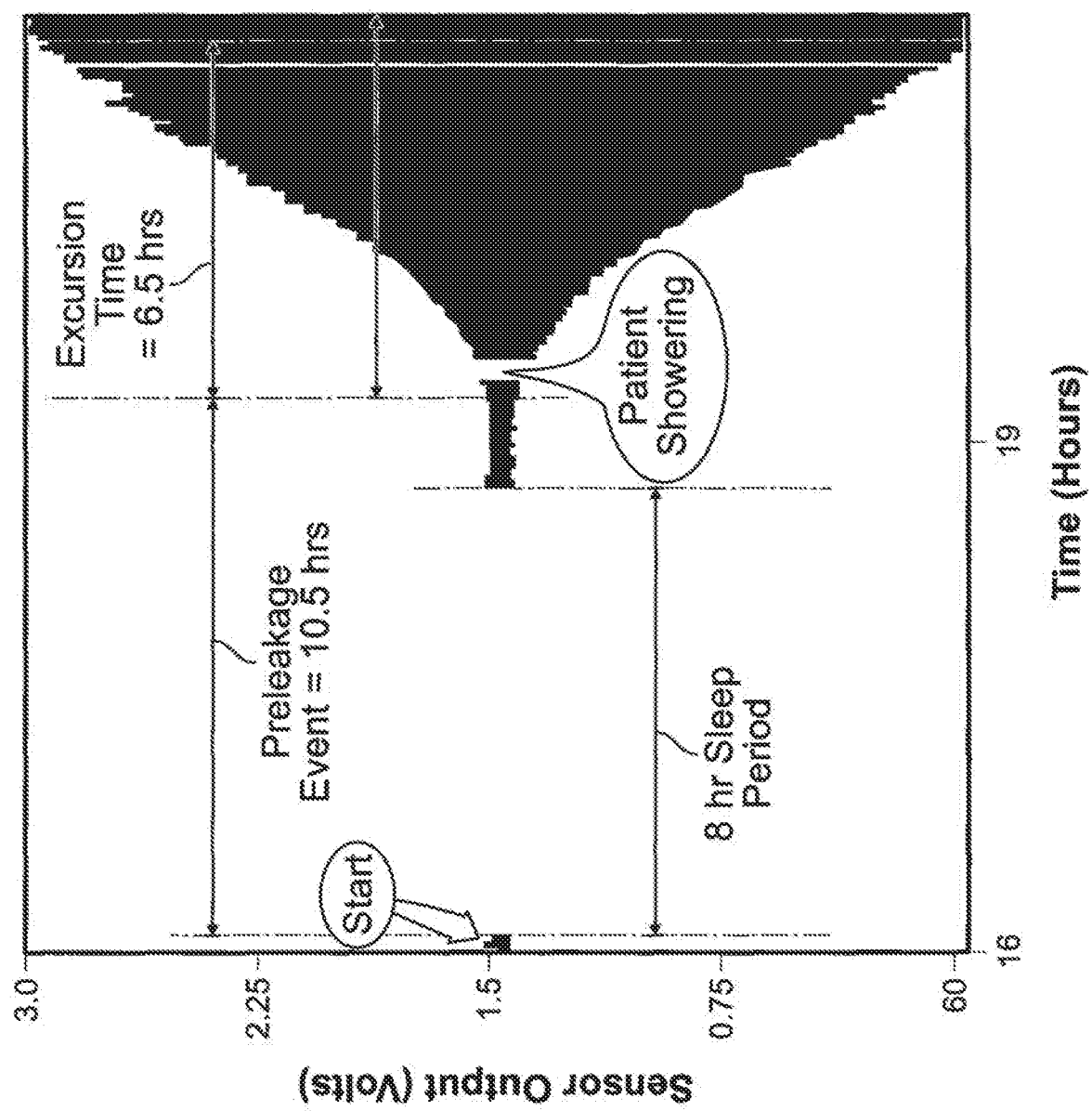
FIGS. 20 and 21 show leakage sensor data according to one data collection method.
Figure 21:
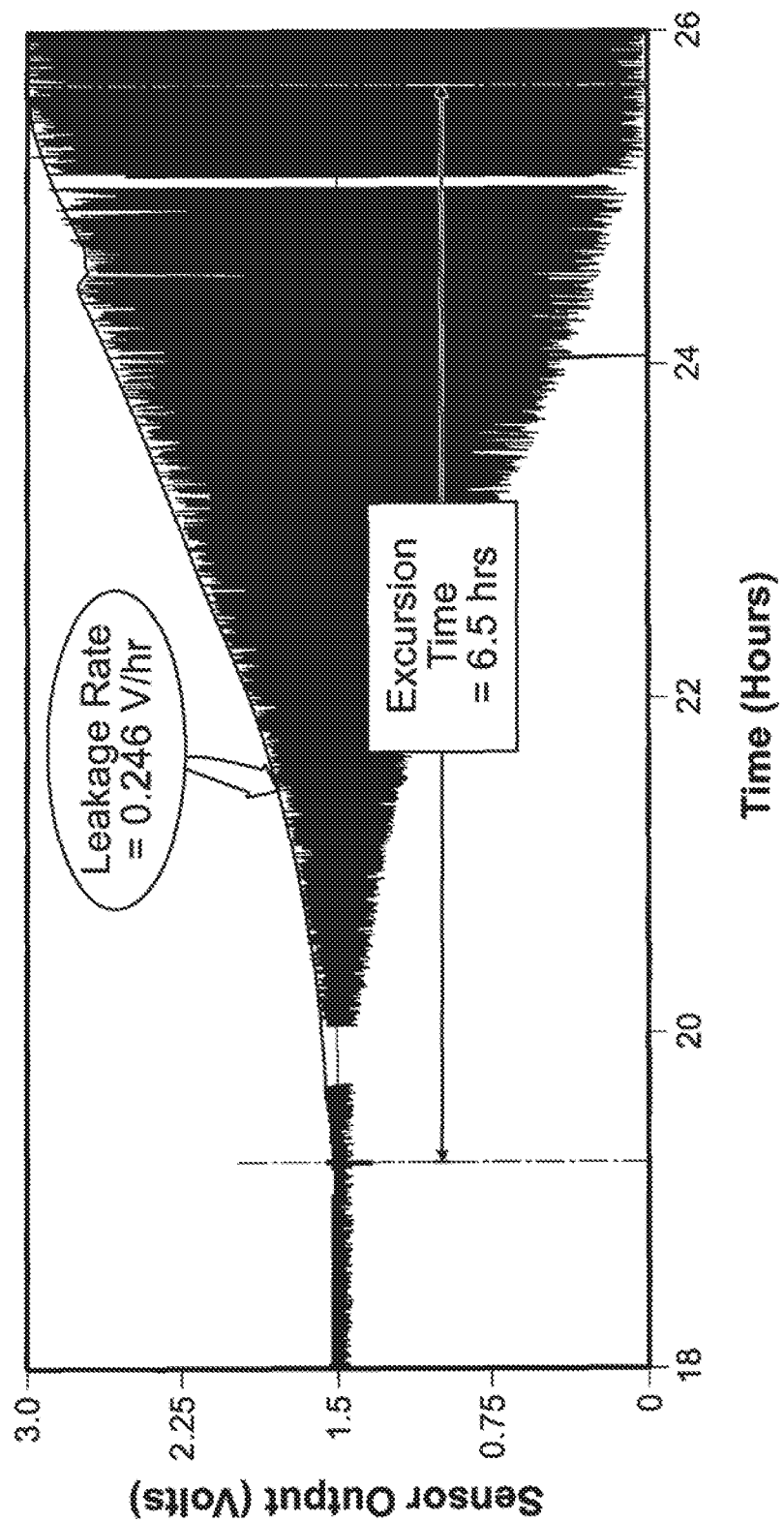

FIGS. 20 and 21 show leakage sensor data collected using a thermoresponsive skin barrier appliance 1000 as described herein on a 37 year-old female ileostomy patient. The appliance 1000 was applied to the ostomy site of the patient and monitored for leakage as described herein. For this test subject, a total of 192.6 hours of test data were collected, where the results indicated a pre-leakage indicator (marked by the 'Start' balloon in FIG. 20), a pre-leakage event of 10.5 hours in duration (data recorder was not worn by patient during 8 hour sleeping period, so a gap in data output occurred), and a leakage event interval of 6.5 hours with a leakage rate of 0.246 volts/hour was detected.

In general, an appliance 1000 of the type described herein can be thermoresponsive to barrier leakage by analyzing and monitoring one or more aspects of leakage sensor data. For example, the control module 1600 can collect leakage sensor data continuously, or at specified intervals, e.g., one data point per minute, over a selected period of time. The control module 1600 can be configured to analyze those data, seeking trends indicative of an impending ostomy leak or a leak that is occurring. For example, the control module 1600 can fit the collected data seeking pre-leakage indicators such as those exemplified in FIGS. 18-21 and for leakage event data generally following an exponential growth. In one approach of many possibilities, the control module 1600 can be programmed to initiate the expulsion of biosealant from one or more micropumps 100 of the appliance 1000 as described herein if a pre-leakage indication has been detected and the leakage sensor data indicate a subsequent exponential rise. In a related approach, the threshold may be met by defining a threshold rate of exponential growth, e.g., a rate greater than 0.1 volts/hour, 0.2 volts/hour, etc., which can be calculated by the control module 1600.

In one exemplary embodiment, a method for thermoresponsively alerting an ostomy patient of an impending stoma leak is provided. The method furthermore provides for controlling the leakage of stoma effluent using an assembly of the type described herein, e.g., assembly 1000.

Figure 22:
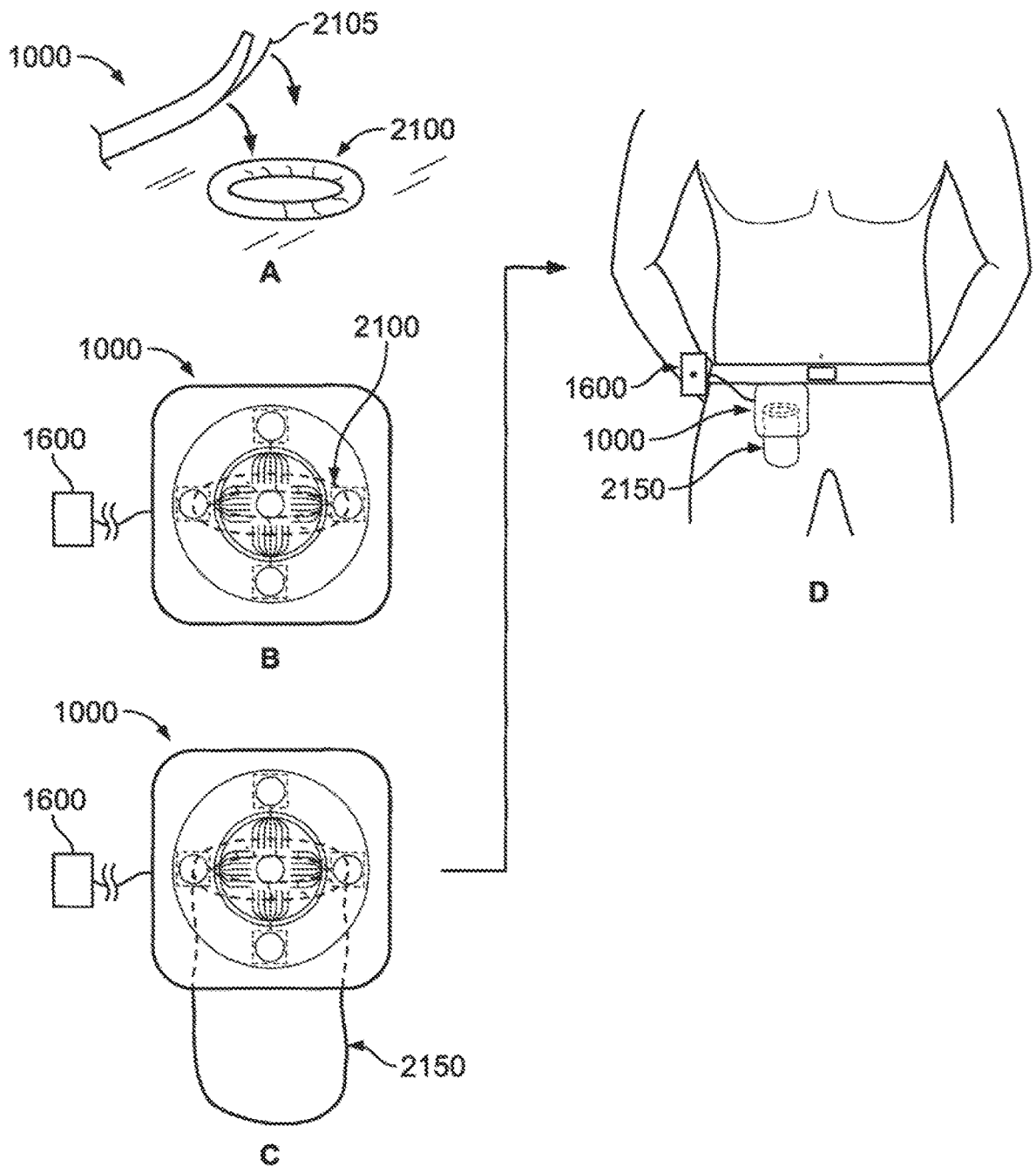
FIGS. 22 and 23 illustrate use of a thermoresponsive skin barrier appliance according to one method.

Referring to FIG. 22, a series of illustrations A-D are shown. Illustration A shows an ostomy stoma 2100 disposed in the abdominal wall of the patient. In this example, the ostomy stoma has no other appliances attached to it to collect effluent. The appliance wafer 1010 can include a peel-off protective layer 2015 that, when removed, exposes an adhesive bottom side of a hydrocolloid layer as described herein. The appliance wafer 1010 can be positioned such that its central opening is placed concentrically over the ostomy stoma 2100.

Referring to illustration B in FIG. 22, the appliance wafer 1010 is shown attached to the patient's skin such that the stoma opening of the appliance wafer and the stoma 2100 are concentrically aligned. Portions of the appliance wafer 1010 surrounding the stoma 2100 may be firmly pressed into place in order to affect a good seal between the hydrocolloid layer and the peristomal skin surrounding the stoma 2100.

Next, referring to illustration C, an ostomy bag 2150 or other article for collecting effluent from the ostomy is attached to the appliance wafer 1010. For example, the ostomy bag 2150 can include a snap-ring having male interlocking components, and the substrate platform (e.g., substrate platform 1060) of the appliance wafer 1010 can be configured to lockingly and sealingly engage the male interlocking components of the ostomy bag snap ring to form a seal therebetween.

Next, referring to illustration D in FIG. 22, the patient can attach a control module, e.g., control module 1600 as previously described. The control module can be worn on clothing articles such as a belt, as shown.

Figure 23:
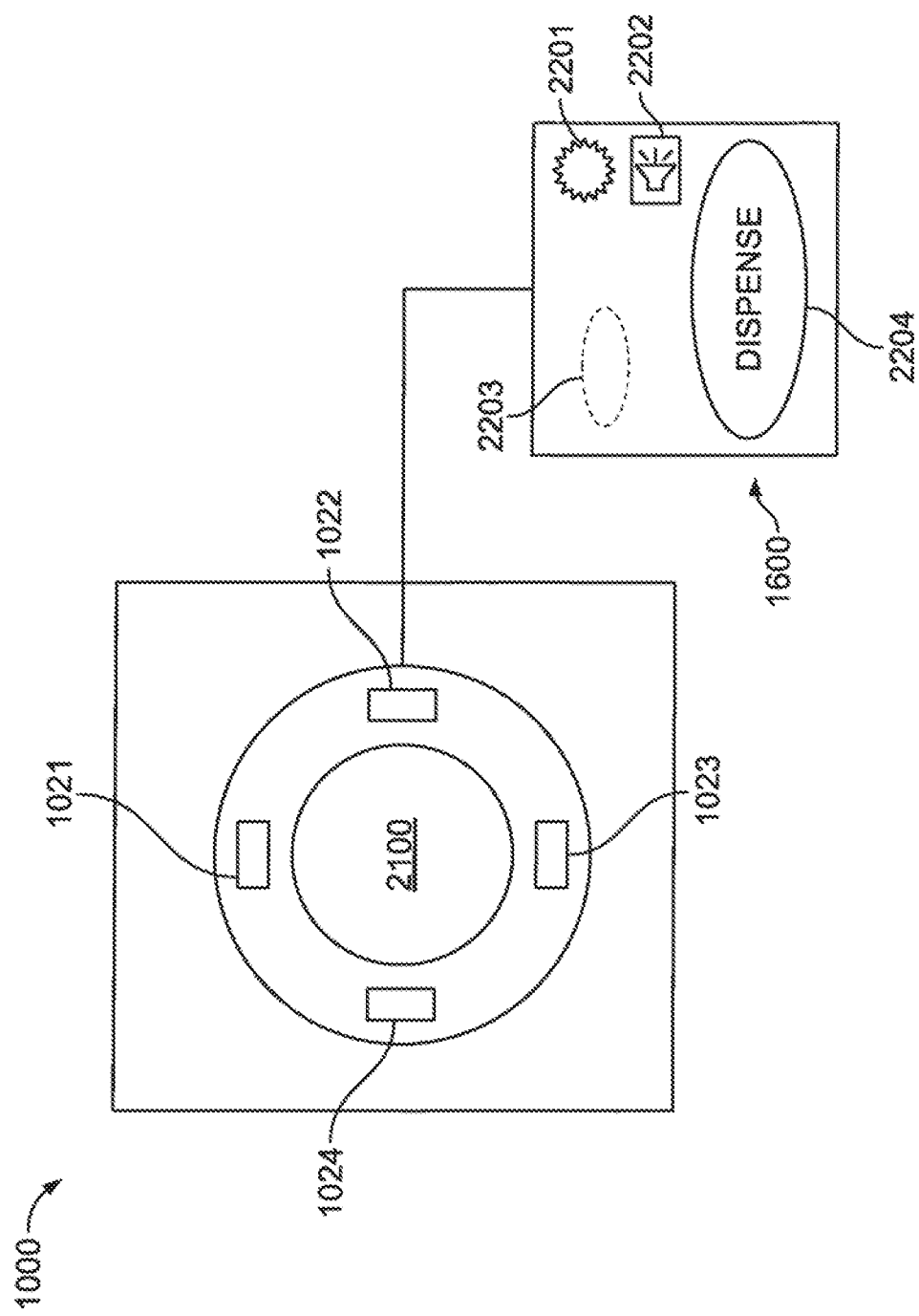

Referring to FIG. 23, the patient may go about his daily routines. In some situations, the bonding between the appliance 1000 and the ostomy stoma 2100 may be effective to prevent leakage from occurring altogether. However, leaks may occur, and in such a situation, the control module 1600 can preemptively alert the patient. In this example, the appliance wafer 1010 is connected to the control module 1600 by an electronic cable interfaced with the leakage sensor. The control module can include a variety of mechanisms to draw attention to the impending leakage event. For example, a visual alert indicator 2201 can include a flashing LED light; an auditory indicator 2202 can sound an audible alarm; or a tactile indicator, in this case, a piezoelectric buzzer 2203 can cause the patient to realize that a leakage event is occurring or will occur in the near future.

At this point, the patient, or the patient's caretaker can take corrective steps to control the leakage event. For example, the patient can push a "Dispense" button 2204 which can cause one or more of the micropumps 1021, 1022, 1023, or 1024 to activate, thus dispensing sealant at or about the ostomy stoma 2100. In this and other embodiments, the control module 1600 and the sensor array 1200 can be configured cooperatively such that the sensor array 1200 reports to the control module the position of the sensor that detected the leak. The control module can further be configured to activate the micropump closest to the reporting sensor or, in other embodiments, activate a plurality of sensors.

Figure 24:
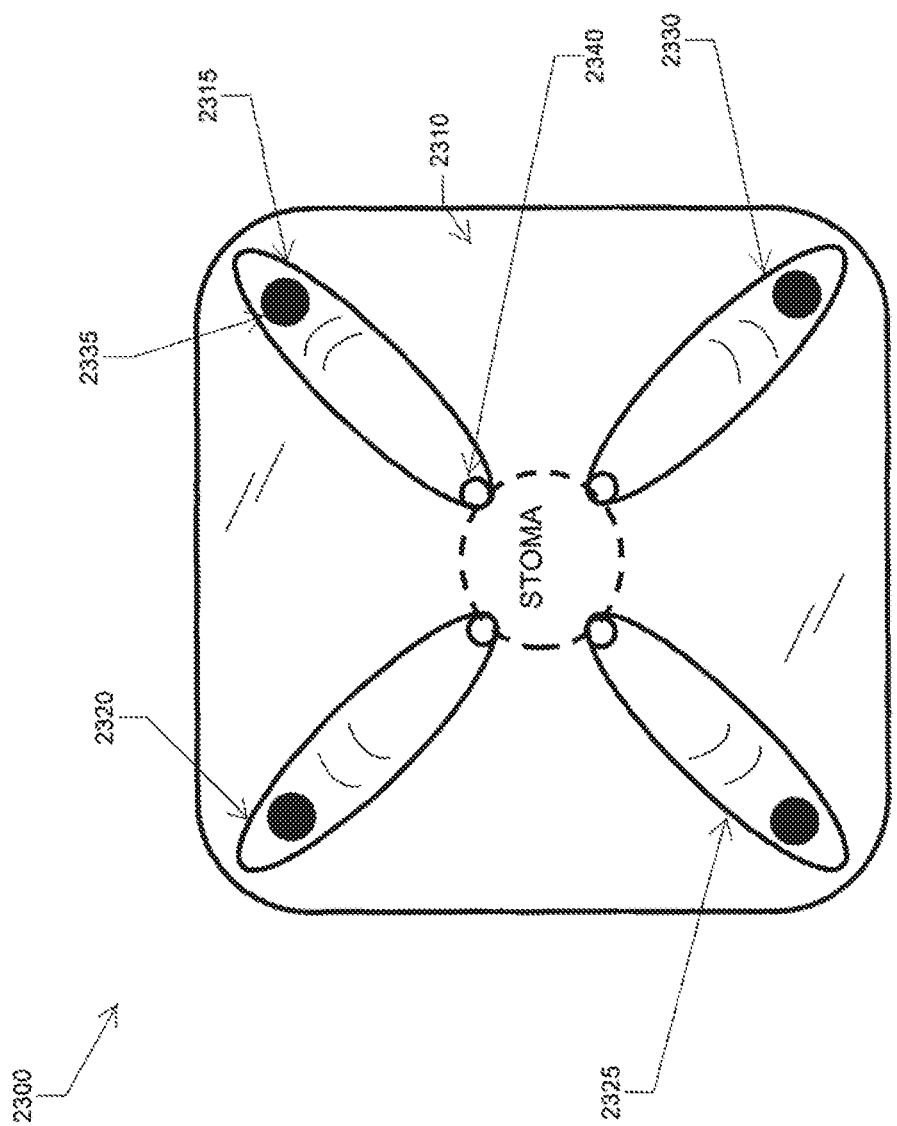
FIG. 24 illustrates a channel substrate of a thermoresponsive skin barrier appliance according to one embodiment.

Referring now to FIG. 24, in one alternative embodiment, microchannels 1040 can be replaced by a fluid-transport channel substrate (hereinafter 'channel substrate') 2300. Channel substrate 2300 can be configured to essentially perform the same function as the microchannels, which is to transport the dispensable fluid 220 from the pump 100 to a treatment area, e.g., a stoma. In this embodiment, channel substrate 2300 is formed by mating top (2310) and bottom (not referenced in FIG. 24) layers of plastic, e.g., polyethylene together in a way which provides fluid transport channels 2315, 2320, 2325 and 2330 as illustrated. Referring to transport channel 2315 in particular, in this embodiment, each fluid transport channel is a semi-flexible pocket having, at a distal end, an input port 2335 configured to receive the dispensable fluid 220 from pump 100. As the dispensable fluid 220 is received by the input port 2335, the transport channel 2315 expands accordingly and directs the dispensable fluid 220 toward output port 2340. Output port 2340 is configured to allow the dispensable fluid 220 to drain about the treatment area, e.g., the stoma area defined by the dashed circular line. While not referenced in FIG. 24 for clarity of the figure, each transport channel 2315, 2320, 2325 and 2330 include an input and output port similar to that described with respect to transport channel 2315.

Channel substrate 2300 can provide an alternative structure for transporting dispensable fluid 220 from pump 100 which may alleviate clogging in embodiments utilizing a microchannel array 1040. While FIG. 24 illustrates four transport channels, it should be understood that any number of transport channels can be employed in any orientation, size or configuration necessary to achieve desired results. In this embodiment, the top (2310) and bottom layers of polyethylene can be mated by, for example, ultrasonic welding techniques, or use of adhesives and transport channels can be formed therein by, e.g., sandwiching a removable, solid substrate between the plastic layers in a preferred orientation and performing the mating of top and bottom polyethylene layers.

Figure 25:
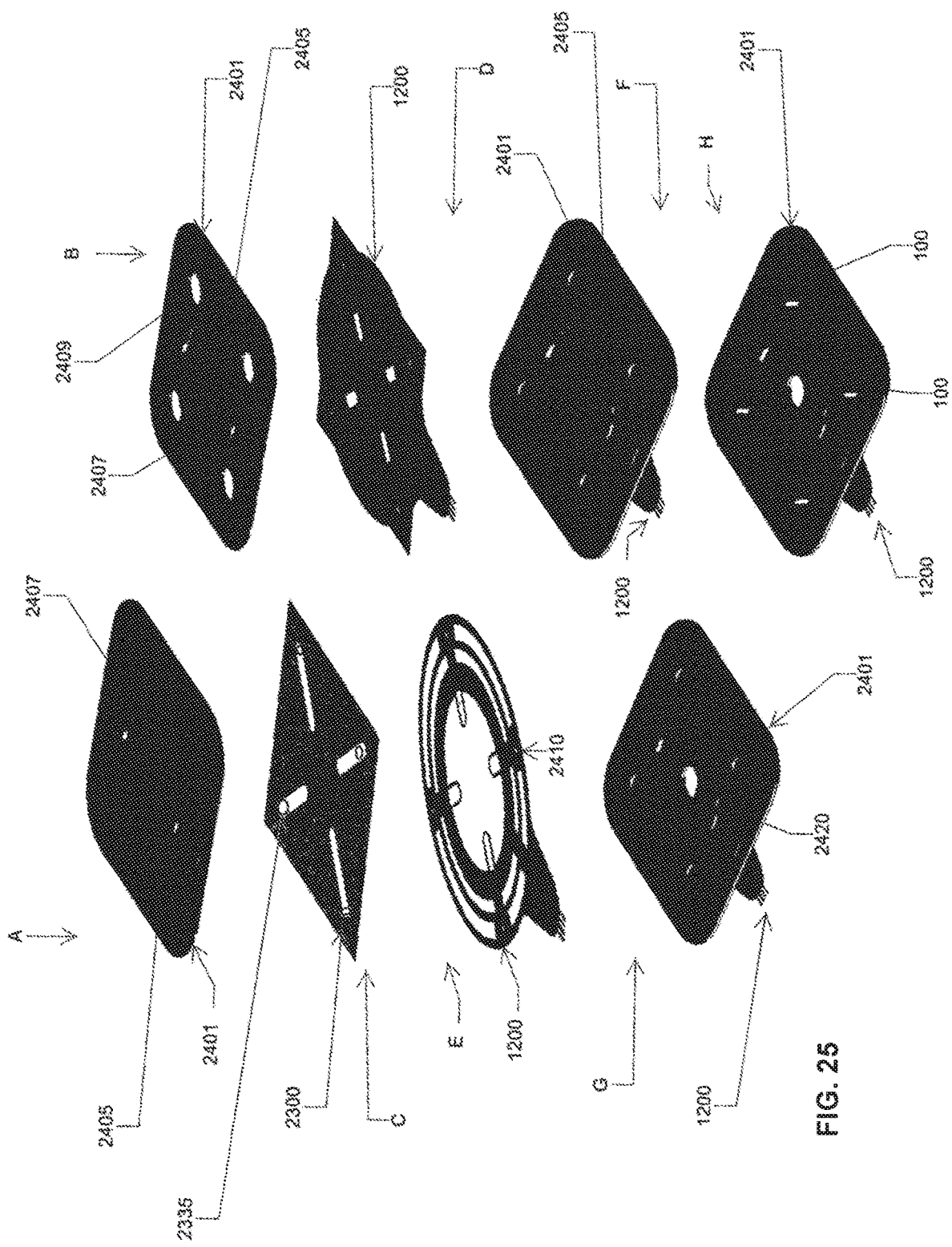
FIG. 25 illustrates an exploded view of a thermoresponsive skin barrier appliance and method of its construction, according to one embodiment.

Referring now to FIG. 25, a method of assembling a thermoresponsive skin barrier appliance is illustrated according to one embodiment. Referring first to frame A, in this embodiment, a polyethylene film (not illustrated) is first applied to an upper side of a top hydrocolloid layer 2405 and a lock ring 2407 is ultrasonically welded thereto as illustrated. The top hydrocolloid layer 2405 and lock ring 2407 are affixed to wafer 2401 which can be, e.g., the same or similar to wafer flange 1020 previously described. Lock ring 2407 can be configured as necessary to provide positive engagement to an ostomy bag or similar item. Next, referring to frame B, a plurality of apertures, e.g., aperture 2409 are cut out of the top hydrocolloid layer 2405 and wafer 2401 which are configured in size and shape to receive a pump, e.g., micropump 100 as described below.

Next, referring to frame C, a channel substrate, e.g., channel substrate 2300 is assembled, e.g., as previously described. At frame D, a leakage sensor circuit, e.g., leakage sensor circuit 1200 is mated to channel substrate 2300 and configured so that the input ports, e.g., input port 2335 of the channel substrate 2300 protrude through corresponding apertures, e.g., aperture 2410 (frame E) of the leakage sensor circuit 1200. In this embodiment, excess channel substrate 2300 material is removed so that the leakage sensor circuit 1200 is not flow-obstructed, e.g., as illustrated in frame E. so that the hydrocolloid can absorb the fluid Next, at frame F, are the leakage sensor circuit 1200 (including the mated channel substrate 2300) is placed between opposing top and bottom hydrocolloid layers; this assembly is then mated to the underside of wafer 2401 as illustrated. In this embodiment, the input ports of the channel substrate 2300 are axially aligned with apertures of the leakage sensor circuit, e.g., aperture 2410, which, in turn are axially aligned with apertures in the hydrocolloid layer, e.g., aperture 2409.

Next, at frame G, a center stoma aperture 2420 is disposed substantially in the center of the device as illustrated. At frame H, a micropump, e.g., micropump 100 is disposed over each aperture in the hydrocolloid layer, e.g., aperture 2409 and configured so that the pump output port, e.g., output port 116 is in fluid communication with input port 2335 of channel substrate 2300.

In the foregoing example, it should be understood that various micropumps can be used for supplying a sealing or treatment fluid or other substance to the input port of channel substrate 2300. Exemplary micropumps include micropumps 100, 200 as described herein, including the various embodiments and alternative structures described. In these cases, the output ports 116, 216 of micropumps 100, 200 respectively can be coupled to input ports 2335 using, e.g., direct connections, tubing or other fluid connection mechanisms.

In general, the output flow rate of a micropump, e.g., micropump 100 or 200 can be controlled by selection of polymer layer 140 or 240 material, or a property of the polymer layer 140 material. For example, in one embodiment, when the polymer layer 140 or 240 is, or includes a layer of hydrogel beads, the output flow rate of a micropump can be controlled by the amount of moisture present in the hydrogel beads.

Figure 26:
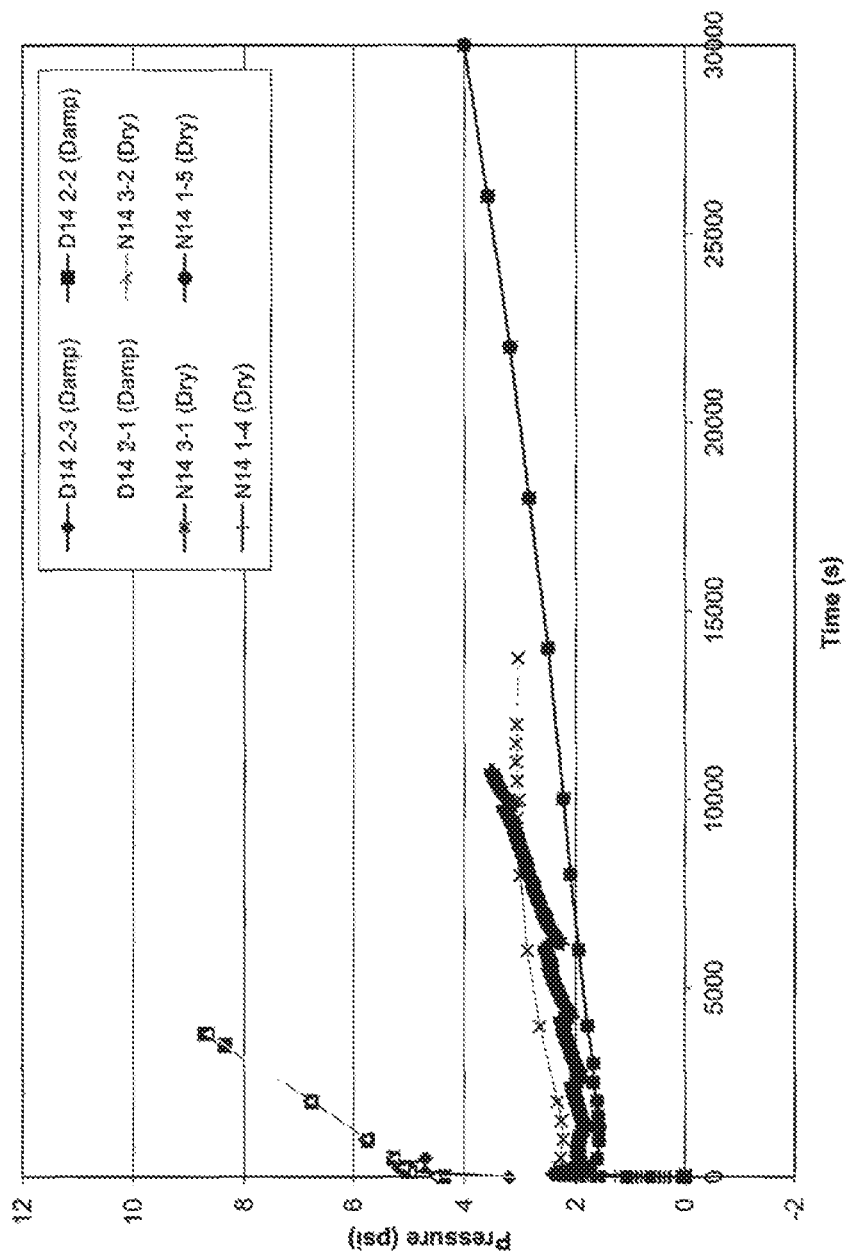
FIG. 26 is a chart illustrating micropump output pressure vs. time for a series of hydrogel plug layer samples having different moisture content.

Referring to FIG. 26 and data presented in TABLE 1 (FIG. 27), it is shown that hydrogel beads having at least some moisture content, i.e., prior to being exposed to the activation solution, results in a faster, higher pressure pump output rate than dry hydrogel beads. For example, the pump pressure over time for samples D142-3, D142-1 and D142-2 in FIG. 26 show a rapid output rate compared to the other samples (indicated as ("Dry")), which exhibit a slower, more gradual output pressure.

Thus, in this embodiment, a micropump output rate can be selectively controlled by incorporating a hydrogel plug layer having a chosen degree of moisture. Without wishing to be bound by theory, it is postulated that hydrogel beads are substantially porous structures, and that by keeping at least some level of moisture within the beads, the activation solution is allowed to penetrate the beads faster, which corresponds to faster swelling and hence, an increased pump output rate compared to dry hydrogel beads.

Utilizing this information, a thermoresponsive skin barrier appliance can be used to provide rapid or slower delivery of a treatment substance. For example, a thermoresponsive skin barrier appliance can include moist hydrogel beads as the polymer layer 140 or 240 to provide rapid sealing of, e.g., an ostomy leak when the treatment substance is a sealant. Conversely, a thermoresponsive skin barrier appliance can include dry hydrogel beads as the polymer layer 140 or 240 when longer, more gradual application of the treatment substance is desired, e.g., in the case of delivering a pharmacological agent to a wound or during prolonged drug delivery to a patient.

A number of illustrative embodiments have been described. Nevertheless, it will be understood that various modifications may be made without departing from the spirit and scope of the various embodiments presented herein. For example, an appliance as described herein, e.g., appliance 1000 can be used to treat various types of wounds, lesions, or other physiological abnormalities other than ostomies. For example, in one embodiment, micropumps in an appliance can be configured to deliver a selected amount of a chemotherapy agent, antiseptic, antibiotic, growth factor, or other wound care therapy agent. The wound therapy agent can be dispensed at a rate of microliters to milliliters per hour. In one embodiment, an appliance can be used cooperatively with negative pressure wound therapy (or without if the amount of chemotherapy agent is small). Accordingly, other embodiments are within the scope of the following claims.

What is claimed is:

1. A skin barrier appliance, comprising:
 a substrate comprising top and bottom surfaces and a central aperture, said substrate being disposed between upper and lower hydrocolloid layers;
 a first moisture sensor disposed on said top surface of said substrate; and
 a second moisture sensor disposed on said bottom surface of said substrate;
 wherein each of said first and said second moisture sensors are configured to detect effluent and send an activation signal to a pump containing a flowable substance upon the detection of said effluent; and
 wherein said first moisture sensor is configured to detect effluent flow in a radial direction from said central aperture, parallel to said top surface of said substrate, and said second moisture sensor is configured to detect effluent flow orthogonal to said bottom surface of said substrate.

2. The skin barrier appliance of claim 1, wherein said moisture sensor comprises a plurality of electrochemical sensors configured to detect said effluent.

3. The skin barrier appliance of claim 1, wherein said flowable substance comprises a sealant or a therapeutic compound.

4. The skin barrier appliance of claim 1, further comprising a microchannel array configured to provide a flow path for said flowable substance between an output of said pump and a target delivery area.

5. A skin barrier appliance, comprising:
 a moisture sensor disposed between upper and lower hydrocolloid layers configured to detect moisture and send an activation signal to a pump containing a flowable substance upon the detection of said moisture; and
 an expandable fluid delivery channel formed from at least two overlapping sheets of a polymeric material;
 wherein said moisture sensor is configured to detect moisture flow in either of two substantially orthogonal moisture flow directions.

6. The skin barrier appliance of claim 5, wherein a proximal end portion of said fluid delivery channel comprises an input port for receiving said flowable substance, and a distal end portion of said fluid delivery channel comprises an output port for dispensing said flowable substance onto a target area.

7. The skin barrier appliance of claim 1, further comprising a user-activated control module for activating said pump to expel said flowable substance on demand.

* * * * *